US008999348B2

(12) United States Patent
Wald et al.

(10) Patent No.: US 8,999,348 B2
(45) Date of Patent: Apr. 7, 2015

(54) VARIANTS OF GROUP 6 ALLERGENS OF THE TRUE GRASSES HAVING REDUCED ALLERGENEITY DUE TO MUTAGENESIS OF PROLINE RESIDUES

(75) Inventors: Martin Wald, Hamburg (DE); Andreas Nandy, Hamburg (DE); Helmut Fiebig, Schwarzenbek (DE); Bernhard Weber, Hamburg (DE); Helga Kahlert, Hamburg (DE); Gerald Reese, Langen (DE); Oliver Cromwell, Suesel-Fassenberg (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/522,041

(22) PCT Filed: Dec. 17, 2010

(86) PCT No.: PCT/EP2010/007745

§ 371 (c)(1),
(2), (4) Date: Jul. 13, 2012

(87) PCT Pub. No.: WO2011/085782

PCT Pub. Date: Jul. 21, 2011

(65) Prior Publication Data

US 2013/0224251 A1 Aug. 29, 2013

(30) Foreign Application Priority Data

Jan. 14, 2010 (EP) .................................... 10000293

(51) Int. Cl.

| | |
|---|---|
| ***A61K 38/00*** | (2006.01) |
| ***A61K 39/00*** | (2006.01) |
| ***A61K 39/35*** | (2006.01) |
| ***A61K 39/36*** | (2006.01) |
| ***C07K 14/415*** | (2006.01) |
| ***A61K 45/06*** | (2006.01) |

(52) U.S. Cl.

CPC ............... *C07K 14/415* (2013.01); *A61K 39/36* (2013.01); *A61K 39/00* (2013.01); *A61K 45/06* (2013.01); *A61K 2039/53* (2013.01); *C07K 2319/21* (2013.01); *A61K 38/00* (2013.01)

(58) Field of Classification Search

None

See application file for complete search history.

(56) References Cited

FOREIGN PATENT DOCUMENTS

WO WO 01/30816 A1 5/2001

OTHER PUBLICATIONS

Mukherjee et al. 'Allergic Asthma: Influence of Genetic and Environmental Factors.' The Journal of Biological Chemistry vol. 286(38):32883-32889, 2011.*

Blumenthal et al. 'Definition of an Allergen.' Allergens and Allergen Immunotherapy. Ed. R Lockey, S. Bukantz and J. Bousquet. New York: Marcel Decker, 2004.37-50.*

Wald et al. 'Recombinant hypoallergenic variants of Phl p 6: candidates for allergen-specific immunotherapy.' Allergy. 65(Suppl. 92):256-257, 2010.*

International Search Report of PCT/EP2010/007745 (Apr. 5, 2011).

S. Vrtala et al., "Genetic Engineering of the Major Timothy Grass Pollen Allergen, Phl p 6, to Reduce Allergenic Activity and Preserve Immunogenicity", The Journal of Immunology, vol. 179, No. 3 (Aug. 1, 2007) pp. 1730-1739.

S. Vrtala et al., "Molecular, Immunological, and Structural Characterization of Phl p 6, A Major Allergen and P-Particle-Associated Protein from Timothy Grass (*Phleum pratense*) Pollen", Journal of Immunology, vol. 163, No. 10 (Nov. 1, 1999) pp. 5489-5496.

L.K. James et al. "Update on Mechanisms of Allergen Injection Immunotherapy", Clinical and Experimental Allergy, vol. 38, No. 7 (Jul. 2008) pp. 1074-1088.

R. Valenta et al., "Recombinant Allergens for Immunotherapy", Journal of Allergy and Clinical Immunology, vol. 119, No. 4 (Apr. 5, 2007) pp. 826-830.

T. Takai et al., "Effects of Proline Mutations in the Major House Dust Mite Allergen Der f 2 on IgE-Binding and Histamine-Releasing Activity", European Journal of Biochemistry, vol. 267, No. 22 (Nov. 2000) pp. 6650-6656.

P.L. Bhalla et al., "Biotechnology-Based Allergy Diagnosis and Vaccination", Trends in Biotechnology, vol. 26, No. 3 (Jan. 28, 2008) pp. 153-161.

B. Linhart et al., "A Hypoallergenic Hybrid Molecule with Increased Immunogenicity Consisting of Derivatives of the Major Grass Pollen Allergens, Phl p 2 and Phl p 6", Biological Chemistry, vol. 389, No. 7 (Jul. 1, 2008) pp. 925-933.

* cited by examiner

*Primary Examiner* — Nora Rooney

(74) *Attorney, Agent, or Firm* — Millen, White, Zelano & Branigan, P.C.

(57) ABSTRACT

The present invention relates to the preparation and use of recombinant variants of group 6 allergens of the Poaceae (true grasses), which are characterized by reduced IgE reactivity compared with known wild-type allergens and at the same time substantially retained reactivity with T-lymphocytes.

10 Claims, 13 Drawing Sheets

Fig. 1: Alignment of deduced amino acid sequences of group 6 and group 5 allergens of Timothy grass

```
                                   Helix 1
1    G K A T T E E Q K L I E D V N A S F R A A M A T T A   Phl p 6.0101
1    G K A T T E E Q K L I E D I N A S F R A A M A T T A   Phl p 6.0102
32   G K A T T E E Q K L I E K I N A G F K A A L A A A A   Phl p 5.0101
21   G K A T T E E Q K L I E K I N D G F K A A L A A A A   Phl p 5.0104
29   G K A T T E E Q K L I E K I N A G F K A A L A A A A   Phl p 5.0109
18   S K A T T E E Q K L I E D I N V G F K A A V A A A A   Phl p 5.0201

                                   Helix 2
         29 30
27   N V P P A D K Y K T F E A A F - - - - - - - - - - -   Phl p 6.0101
27   N V P P A D K Y K T F E A A F - - - - - - - - - - -   Phl p 6.0102
58   G V Q P A D K Y R T F V A T F G A A S N K A F A E G   Phl p 5.0101
47   G V P P A D K Y K T F V A T F G A A S N K A F A E G   Phl p 5.0104
55   G V P P A D K Y R T F V A T F G A A S N K A F A E G   Phl p 5.0109
44   S V P A A D K F K T F E A A F - - - - - - - - - - -   Phl p 5.0201

                             Helix 2
                                                 57
42   - - - - - - - - - T V S S K R N L A D A V S K A P Q   Phl p 6.0101
42   - - - - - - - - - T V S S K R N L A D A V S K A P Q   Phl p 6.0102
84   L S G E P K G A A E S S S K A A - - - - - - - - - -   Phl p 5.0101
73   L S A E P K G A A E S S S K G A - - - - - - - - - -   Phl p 5.0104
81   L S G E P K G A A E S S S K A A - - - - - - - - - -   Phl p 5.0109
59   - - - - - - - - - T S S S K A A A A - - - - K A P G   Phl p 5.0201

                       Helix 3
         61                                  79
59   L V P K L D E V Y N A A Y N A A D H A A P E D K Y E   Phl p 6.0101
59   L V P K L D E V Y N A A Y N A A D H A A P E D K Y E   Phl p 6.0102
100  L T S K L D A A Y K L A Y K T A E G A T P E A K Y D   Phl p 5.0101
89   L T S K L E A A Y K L A Y K T S E G A T P E A K Y D   Phl p 5.0104
97   L T S K L D A A Y K L A Y K T A E G A T P E A K Y D   Phl p 5.0109
72   L V P K L D A A Y S V A Y K A A V G A T P E A K F D   Phl p 5.0201

                      Helix 4
                                   101           108
85   A F V L H F S E A L R I I A G T P E V H A V K P G A   Phl p 6.0101
85   A F V L H F S E A L H I I A G T P E V H A V K P G A   Phl p 6.0102
126  A Y V A T L S E A L R I I A G T L E V H A V K P A A   Phl p 5.0101
115  A Y V A T L S E A L R I I A G T L E V H A V K P A A   Phl p 5.0104
123  A Y V A T L S E A L R I I A G T L E V H A V K P A A   Phl p 5.0109
98   S F V A S L T E A L R V I A G A L E V H A V K P V T   Phl p 5.0201
```

```
85   A F V L H F S E A L R I I A G T P E V H A V K P G A   Phl p 6.0101
85   A F V L H F S E A L H I I A G T P E V H A V K P G A   Phl p 6.0102
126  A Y V A T L S E A L R I I A G T L E V H A V K P A A   Phl p 5.0101
115  A Y V A T L S E A L R I I A G T L E V H A V K P A A   Phl p 5.0104
123  A Y V A T L S E A L R I I A G T L E V H A V K P A A   Phl p 5.0109
98   S F V A S L T E A L R V I A G A L E V H A V K P V T   Phl p 5.0201
```

Alignment of the ripe form of the Phl p 6 isoform used here, Phl p 6.0102 (IUIS sequence, UniprotKB O65868, length 110 amino acids) with the second known Phl p 6 isoform, Phl p 6.0101 (IUIS sequence, UniprotKB P43215, length 110 amino acids) and N-terminal part-regions of four Phl p 5 isoforms: Phl p 5.0101 (IUIS sequence, UniprotKB Q40960), Phl p 5.0104 (IUIS sequence, UniprotKB P93467), Phl p 5.0109 (IUIS sequence, UniprotKB Q84UI2, 284 amino acids) and Phl p 5.0201 (IUIS sequence, UniprotKB Q40963, total length 265 amino acids and). The amino acid position information on the left indicates the position of the amino acid in the processed protein. The position of the seven proline residues present in Phl p 6 is indicated separately above the sequence. The boxes show the position of the $\alpha$-helices of Phl p 6 based on an X-ray structural analysis of a recombinant Phl p 6 (PDB entry 1NLX; Fedorov et al., 2003). Regions having sequence identity to Phl p 6.0102 are highlighted in grey.

Fig. 2: Working model of the 3D structure of Phl p 6

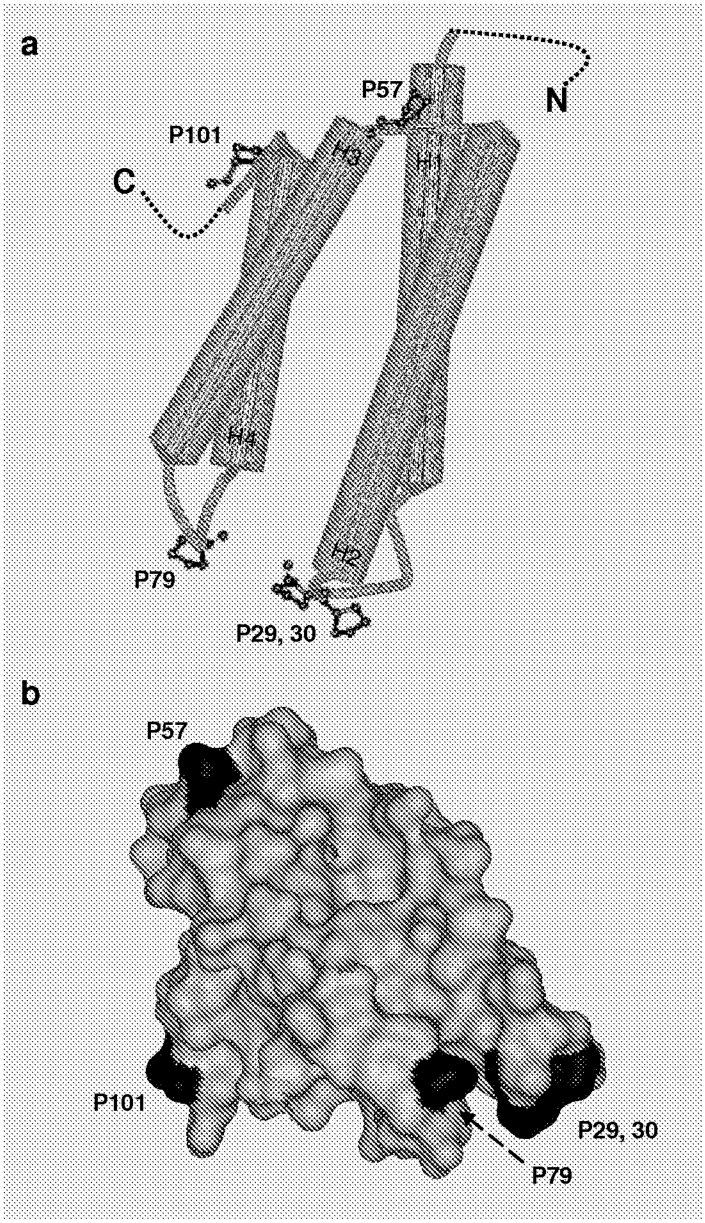

a.) Simplified model of Phl p 6. Four α-helices (H1-H4) form a 4-helix bundle. Proline residues 29, 30, 57 and 79. are present in the loops connecting the helices. Proline 101 is located behind the final helix.

b.) Surface model. Proline residues 29, 30, 57, 79 and 101 are exposed at the surface.

Proline residues are in each case coloured black and provided with position designation. Both models are based on an X-ray structural analysis of a recombinant Phl p 6 (PDB entry: 1NLX; Fedorov et al., 2003)

Fig. 3: Phl p 6 wt (IUIS entry Phl p 6.0102); cDNA sequence (GenBank entry: Y16955; 330 bp); SEQ ID NO:1

GGGAAGGCCACGACCGAGGAGCAAAAATTGATCGAGGACATCAATGCCA
GCTTTAGGGCGGCCATGGCCACCACTGCTAACGTCCCTCCAGCAGACAA
GTATAAGACATTCGAAGCCGCCTTCACGGTGTCCTCAAAGAGAAACCTCG
CTGACGCCGTTTCAAAGGCGCCCCAGCTGGTCCCCAAGCTCGATGAAGT
CTACAACGCCGCCTACAATGCTGCCGATCATGCCGCCCCAGAAGACAAG
TATGAAGCCTTCGTCCTTCACTTTTCCGAGGCTCTCCACATCATCGCCGG
TACCCCCGAGGTCCACGCTGTCAAGCCCGGCGCG

Fig. 4: Phl p 6 wt (IUIS entry Phl p 6.0102); deduced amino acid sequence (UniProtKB entry: O65868; 110 aa); SEQ ID NO:2

GKATTEEQKLIEDINASFRAAMATTANVPPADKYKTFEAAFTVSSKRNLADAV
SKAPQLVPKLDEVYNAAYNAADHAAPEDKYEAFVLHFSEALHIIAGTPEVHAV
KPGA

Fig. 5: N-terminal histidine fusion component; DNA sequence (33 bp); SEQ ID NO:5

ATGCATCACCATCACCATCACGCAGGCGGCGGT

Fig. 6: N-terminal histidine fusion component; amino acid sequence (11 aa); SEQ ID NO:6

MHHHHHHAGGG

Fig. 7: Purity control of recombinant Phl p 6 wild type and Phl p 6 variants with proline deletions in a loop
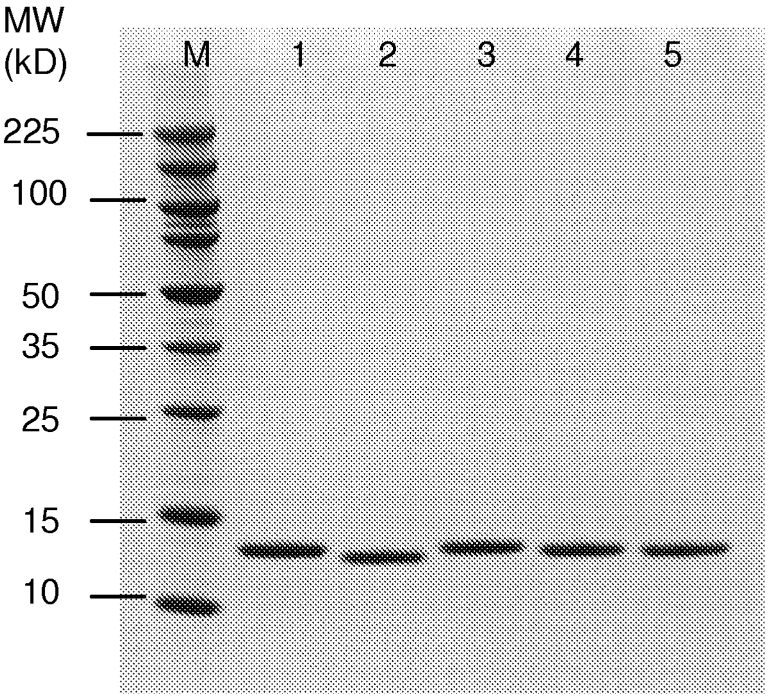
12% SDS-PAGE after Coomassie staining. Charging: ~1 µg of protein per track, non-reduced.
Samples: 1 = rPhl p 6 wt + 6His; 2 = d[P29, 30] + 6His; 3 = d[P57] + 6His; 4 = d[P79] + 6His; 5 = d[P101] + 6His. M: size marker.

Fig. 8: Determination of the molecular weight of Phl p 6 variants with proline mutations in a loop

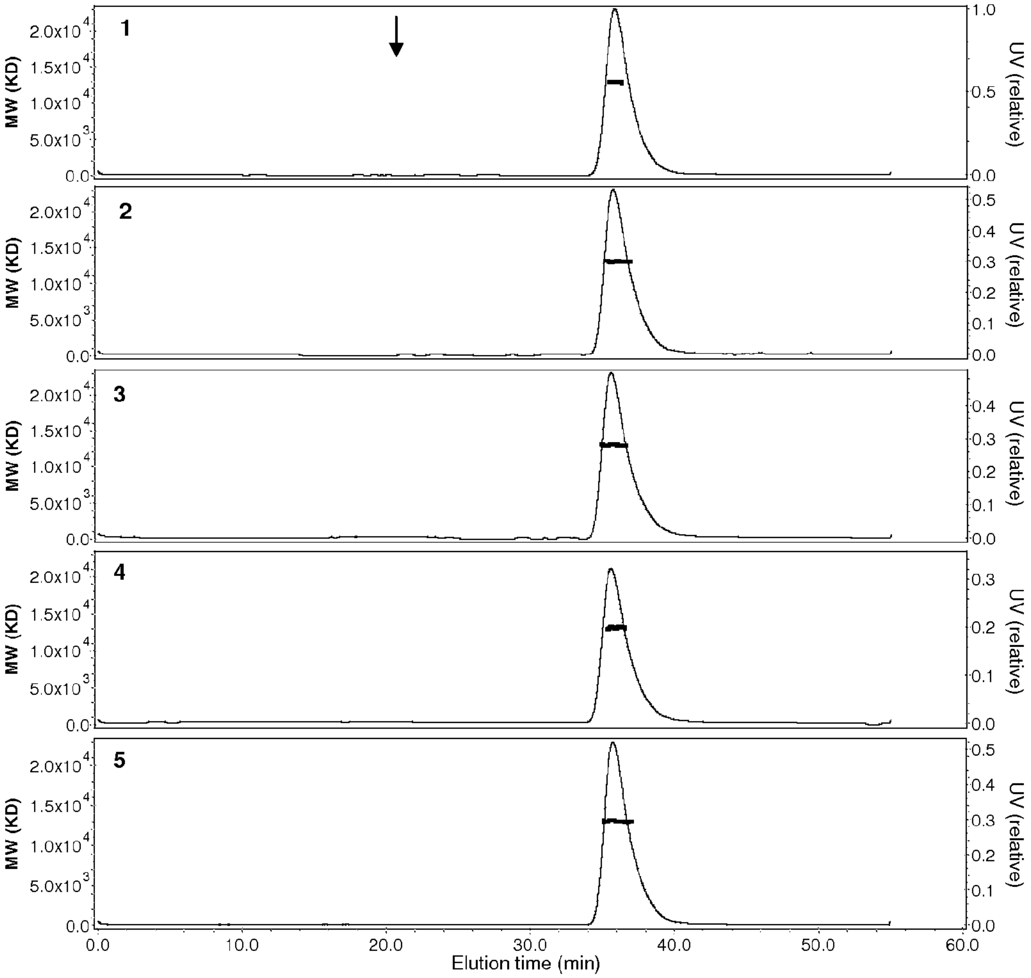

Chromatogram of an analytical SEC with online molecular weight determination.

The figure shows the relative UV signal at 280 nm (right-hand Y axis) and the molecular weight (left-hand Y axis; measurement point line in the peak region), plotted against the elution time (X axis). The online determination of the protein concentration was carried out using the OptilabrEX (Wyatt, Santa Barbara, USA) refractive index detector. The light scattering by the particles was determined using the MiniDAWN Treos multiangle detector (Wyatt). The particle mass was calculated using ASTRA 5.3.2.17 software (Wyatt) via Debeye formalism with a refractive index increment of 0.180 ml/ g. Column: Superdex 200 GL 10/ 300 (GE Healthcare, Uppsala, Sweden). The size exclusion is at 20.45 min (arrow). Eluent: 20 mM Tris, pH 8.0 with 150 mM NaCl Samples: 1 = rPhl p 6 wt + 6His; 2 = d[P29, 30] + 6His; 3 = d[P57] + 6His; 4 = d[P79] + 6His; 5 = d[P101] + 6His

Fig. 9: IgE binding of immobilised Phl p 6 variants with proline deletions in a loop

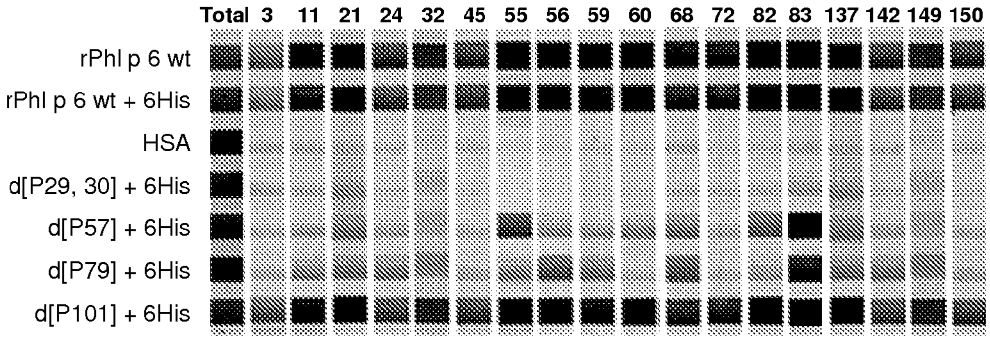

Immunoblot of the test substances after incubation with sera of clinically defined grass pollen allergy sufferers (3-150)

rPhl p 6 wt: recombinant Phl p 6 with (+ 6His) and without histidine fusion component.

HSA: human serum albumin (negative control).
Total: control for uniform protein charging of the test strips. Total protein staining with reagent “DB71” (Sigma-Aldrich, Taufkirchen).

Fig. 10: IgE inhibition test of Phl p 6 variants with proline deletions in a loop

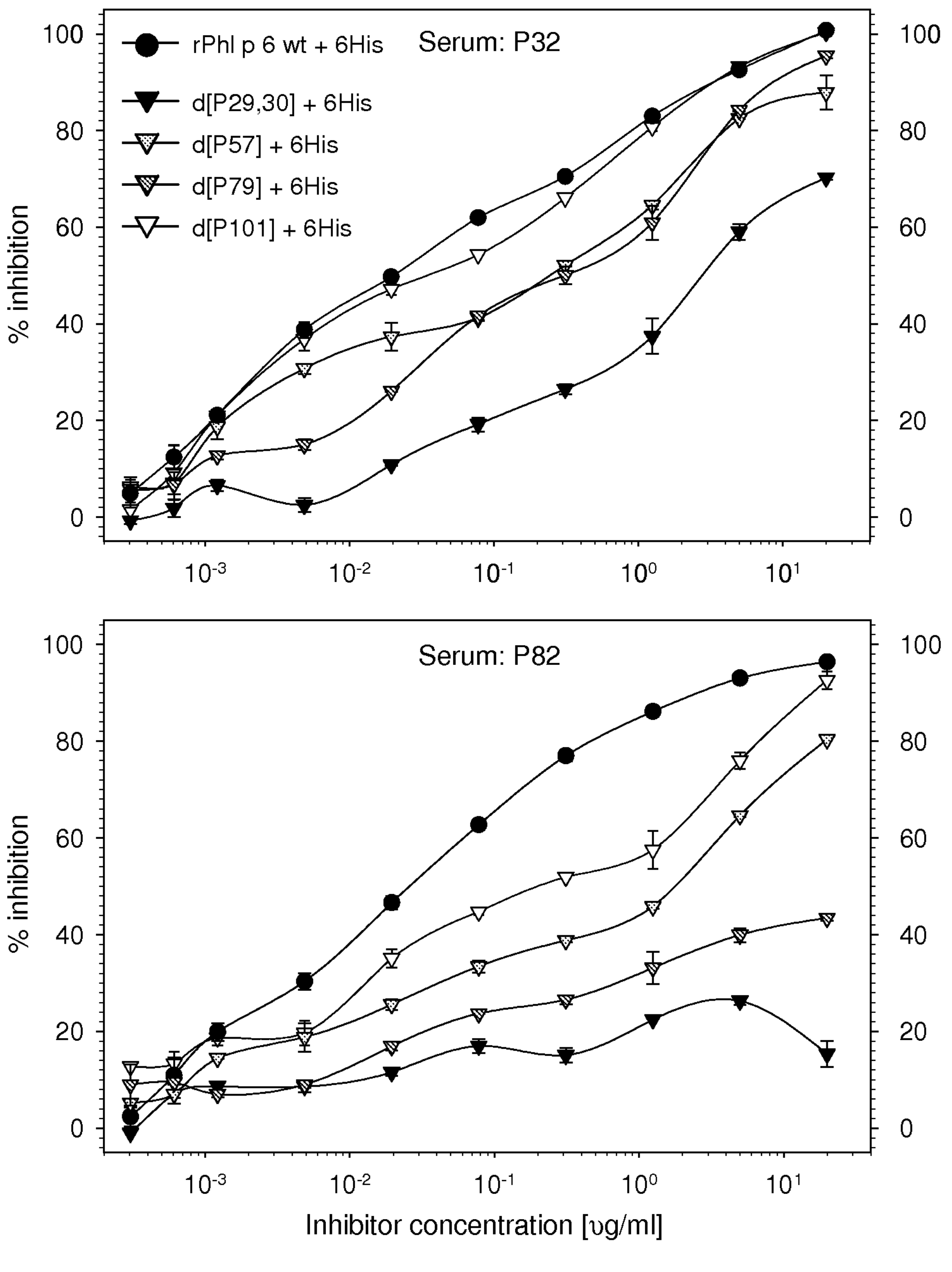

Data from in each case one individual experiment with sera of clinically defined grass pollen allergy sufferers (P). The symbols represent the averages of duplicates on measurement of 10 concentrations of each inhibitor. The horizontal lines of the error bars show the respective individual values of the double determinations. Solid phase: rPhl p 6 wt + 6His.

Fig. 11: Test for functional allergeneity of the proline mutants with mutations in individual loops
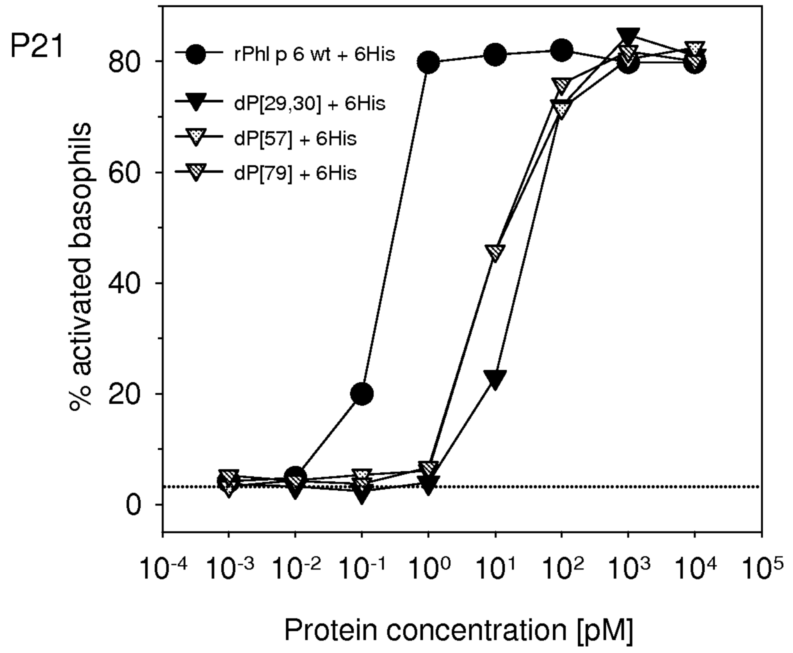
Evidence of reduced functional allergeneity by means of basophil activation test with whole blood of a clinically defined grass pollen allergy sufferer (P21). Horizontal line: level of stimulation by a negative control.

Fig. 12: Purity of Phl p 6 variants with proline mutations in two or three loops: SDS-PAGE
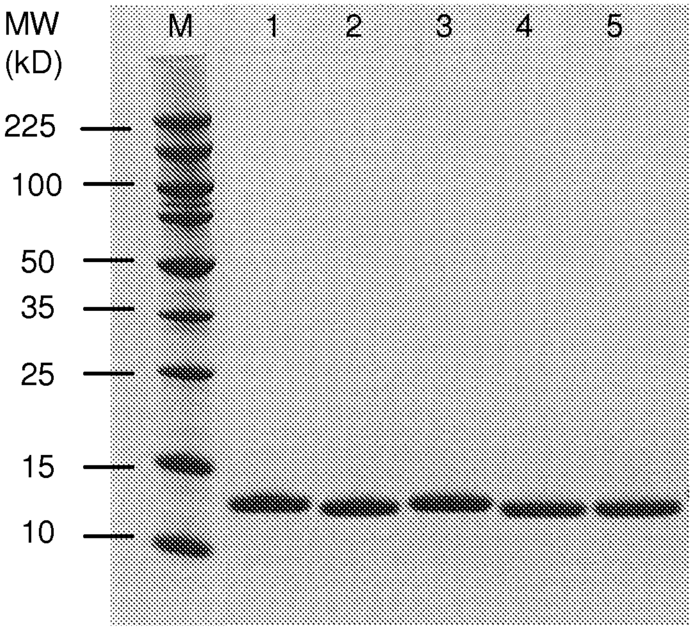
12% SDS-PAGE after Coomassie staining. Charging: ~1 µg of protein per track, non-reduced.
Samples: 1 = d[29, 30, 57] + 6His; 2 = d[P29, 30, 79] + 6His; 3 = d[P29, 30] P57L + 6His; 4 = d[P29, 30] P79L + 6His; 5 = d[P29, 30] P57L, P79L] + 6His.
M: size marker.

Fig. 13: Determination of the molecular weight of Phl p 6 variants with proline mutations in two or three loops

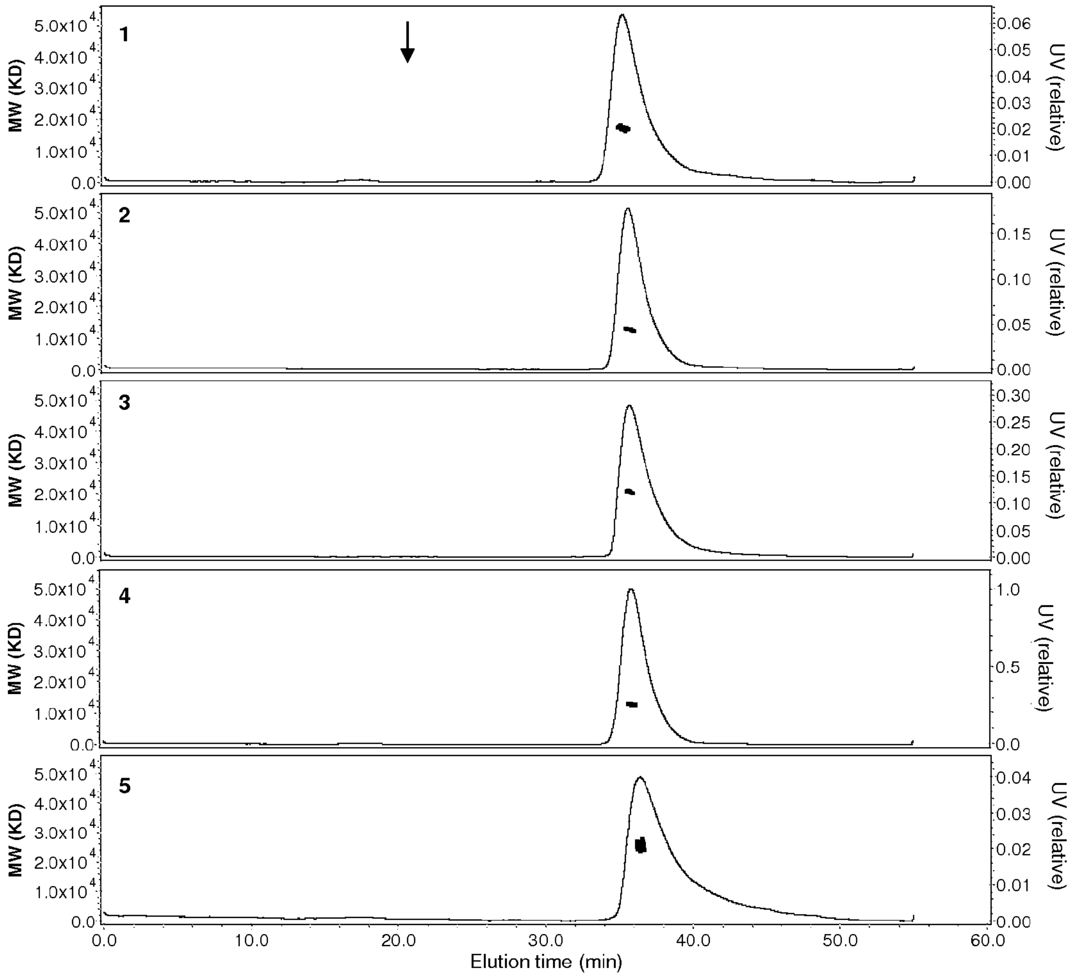

Chromatogram of an analytical SEC with online molecular weight determination.

The figure shows the relative UV signal at 280 nm (right-hand Y axis) and the molecular weight (left-hand Y axis; measurement point line in the peak region), plotted against the elution time (X axis). The online determination of the protein concentration was carried out using the OptilabrEX (Wyatt, Santa Barbara, USA) refractive index detector. The light scattering by the particles was determined using the MiniDAWN Treos multiangle detector (Wyatt). The particle mass was calculated using ASTRA 5.3.2.17 software (Wyatt) via Debeye formalism with a refractive index increment of 0.180 ml/ g.

Column: Superdex 200 GL 10/ 300 (GE Healthcare, Uppsala, Sweden). The size exclusion is at 20.45 min (arrow). Eluent: 20 mM Tris, pH 8.0 with 150 mM NaCl Samples: 1 = d[29, 30, 57] + 6His; 2 = d[P29, 30, 79] + 6His; 3 = d[P29, 30] P57L + 6His; 4 = d[P29, 30] P79L + 6His; 5 = d[P29, 30] P57L, P79L] + 6His

Fig. 14: IgE binding of recombinant Phl p 6 wild type and Phl p 6 variants with proline deletions in one, two or three loops

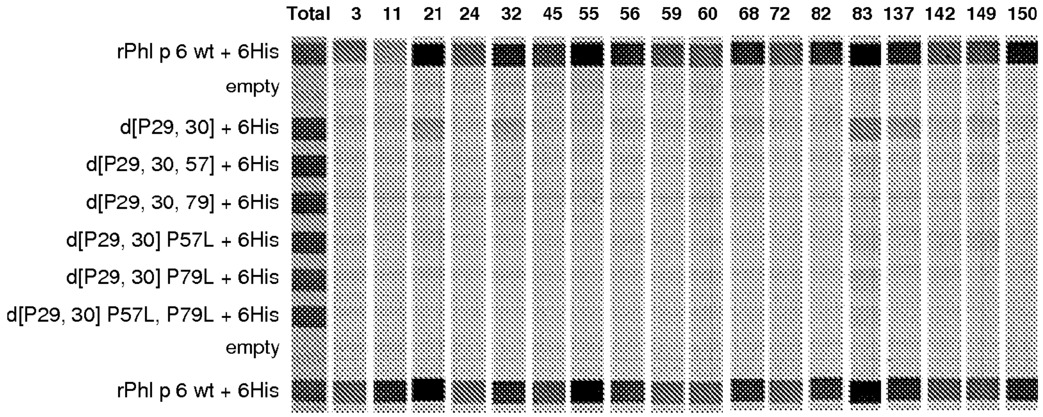

Immunoblot of the test substances after incubation with sera of clinically defined grass pollen allergy sufferers (3-150)

Total: control for uniform protein charging of the test strips. Total protein staining with reagent "DB71" (Sigma-Aldrich, Taufkirchen).

Fig. 15: Phl p 6 wt (IUIS entry Phl p 6.0101); cDNA sequence (GenBank entry: Z27082.1; 330 bp); SEQ ID NO:3

GGGAAGGCCACGACCGAGGAGCAAAAATTGATCGAGGACGTCAATGCCA
GCTTTAGGGCGGCCATGGCCACCACTGCTAACGTCCCTCCAGCAGACAA
GTATAAGACATTCGAAGCCGCCTTCACGGTGTCCTCAAAGAGAAACCTCG
CTGACGCCGTTTCAAAGGCGCCCCAGCTGGTCCCCAAGCTCGATGAAGT
CTACAACGCCGCCTACAATGCTGCCGATCATGCCGCCCCAGAAGACAAG
TATGAAGCCTTCGTCCTTCACTTTTCCGAGGCTCTCCGCATCATCGCCGG
TACCCCCGAGGTCCACGCTGTCAAGCCCGGCGCGTAG

Fig. 16: Phl p 6 wt (IUIS entry Phl p 6.0101); deduced amino acid sequence (UniProtKB entry: P43215; 110 aa); SEQ ID NO:4

GKATTEEQKLIEDVNASFRAAMATTANVPPADKYKTFEAAFTVSSKRNLADA
VSKAPQLVPKLDEVYNAAYNAADHAAPEDKYEAFVLHFSEALRIIAGTPEVHA
VKPGA

Fig. 17: Variant of Phl p 6.0101 (UniProtKB entry O65869; 107 aa), SEQ ID NO:7; the variant is represented by an italic L, the first three amino acids are missing

TEEQKLIEDVNASFRAAMATTANVPPADKYKT*L*EAAFTVSSKRNLADAVSKA
PQLVPKLDEVYNAAYNAADHAAPEDKYEAFVLHFSEALRIIAGTPEVHAVKPG
A

Fig. 18: Variant of Phl p 6.0101 (incl. propeptide), according to our own sequencing. (Propeptide component and Y to H variant bold italics); SEQ ID NO:8

*MAAHKFMVAMFLAVAVVLGLATSPTAEG*GKATTEEQKLIEDVNASFRAAMA
TTANVPPADK*H*KTFEAAFTVSSKRNLADAVSKAPQLVPKLDEVYNAAYNAAD
HAAPEDKYEAFVLHFSEALRIIAGTPEVHAVKPGA

Fig. 19: Pro Phl p 6.0101 (P43215) (propeptide component bold and italics); SEQ ID NO:9

*MVAMFLAVAVVLGLATSPTAEG*GKATTEEQKLIEDVNASFRAAMATTANVP
PADKYKTFEAAFTVSSKRNLADAVSKAPQLVPKLDEVYNAAYNAADHAAPED
KYEAFVLHFSEALRIIAGTPEVHAVKPGA

Fig. 20: Pro Phl p 6.0102 (O65868) (propeptide component bold and italics); SEQ ID NO:10

*MAAHKFMVAMFLAVAVVLGLATSPTAEG*GKATTEEQKLIEDINASFRAAMA
TTANVPPADKYKTFEAAFTVSSKRNLADAVSKAPQLVPKLDEVYNAAYNAAD
HAAPEDKYEAFVLHFSEALHIIAGTPEVHAVKPGA

SEQUENCE LISTING

```
<160> NUMBER OF SEQ ID NOS: 14

<210> SEQ ID NO 1
<211> LENGTH: 330
<212> TYPE: DNA
<213> ORGANISM: Phleum pratense

<400> SEQUENCE: 1

gggaaggcca cgaccgagga gcaaaaattg atcgaggaca tcaatgccag ctttagggcg     60

gccatggcca ccactgctaa cgtccctcca gcagacaagt ataagacatt cgaagccgcc    120

ttcacggtgt cctcaaagag aaacctcgct gacgccgttt caaaggcgcc ccagctggtc    180

cccaagctcg atgaagtcta caacgccgcc tacaatgctg ccgatcatgc cgccccagaa    240

gacaagtatg aagccttcgt ccttcacttt tccgaggctc tccacatcat cgccggtacc    300

cccgaggtcc acgctgtcaa gcccggcgcg                                     330


<210> SEQ ID NO 2
<211> LENGTH: 110
<212> TYPE: PRT
<213> ORGANISM: Phleum pratense

<400> SEQUENCE: 2

Gly Lys Ala Thr Thr Glu Glu Gln Lys Leu Ile Glu Asp Ile Asn Ala
1               5                   10                  15

Ser Phe Arg Ala Ala Met Ala Thr Thr Ala Asn Val Pro Pro Ala Asp
            20                  25                  30

Lys Tyr Lys Thr Phe Glu Ala Ala Phe Thr Val Ser Ser Lys Arg Asn
        35                  40                  45

Leu Ala Asp Ala Val Ser Lys Ala Pro Gln Leu Val Pro Lys Leu Asp
    50                  55                  60

Glu Val Tyr Asn Ala Ala Tyr Asn Ala Ala Asp His Ala Ala Pro Glu
65                  70                  75                  80

Asp Lys Tyr Glu Ala Phe Val Leu His Phe Ser Glu Ala Leu His Ile
                85                  90                  95

Ile Ala Gly Thr Pro Glu Val His Ala Val Lys Pro Gly Ala
            100                 105                 110


<210> SEQ ID NO 3
<211> LENGTH: 333
<212> TYPE: DNA
<213> ORGANISM: Phleum pratense

<400> SEQUENCE: 3

gggaaggcca cgaccgagga gcaaaaattg atcgaggacg tcaatgccag ctttagggcg     60

gccatggcca ccactgctaa cgtccctcca gcagacaagt ataagacatt cgaagccgcc    120

ttcacggtgt cctcaaagag aaacctcgct gacgccgttt caaaggcgcc ccagctggtc    180
```

-continued

```
cccaagctcg atgaagtcta caacgccgcc tacaatgctg ccgatcatgc cgccccagaa    240

gacaagtatg aagccttcgt ccttcacttt tccgaggctc tccgcatcat cgccggtacc    300

cccgaggtcc acgctgtcaa gcccggcgcg tag                                 333


<210> SEQ ID NO 4
<211> LENGTH: 110
<212> TYPE: PRT
<213> ORGANISM: Phleum pratense

<400> SEQUENCE: 4

Gly Lys Ala Thr Thr Glu Glu Gln Lys Leu Ile Glu Asp Val Asn Ala
1               5                   10                  15

Ser Phe Arg Ala Ala Met Ala Thr Thr Ala Asn Val Pro Pro Ala Asp
            20                  25                  30

Lys Tyr Lys Thr Phe Glu Ala Ala Phe Thr Val Ser Ser Lys Arg Asn
        35                  40                  45

Leu Ala Asp Ala Val Ser Lys Ala Pro Gln Leu Val Pro Lys Leu Asp
    50                  55                  60

Glu Val Tyr Asn Ala Ala Tyr Asn Ala Ala Asp His Ala Ala Pro Glu
65                  70                  75                  80

Asp Lys Tyr Glu Ala Phe Val Leu His Phe Ser Glu Ala Leu Arg Ile
                85                  90                  95

Ile Ala Gly Thr Pro Glu Val His Ala Val Lys Pro Gly Ala
            100                 105                 110


<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

atgcatcacc atcaccatca cgcaggcggc ggt                                  33


<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met His His His His His His Ala Gly Gly Gly
1               5                   10


<210> SEQ ID NO 7
<211> LENGTH: 106
<212> TYPE: PRT
<213> ORGANISM: Phleum pratense

<400> SEQUENCE: 7

Thr Glu Glu Gln Lys Leu Ile Glu Asp Val Asn Ala Ser Phe Arg Ala
1               5                   10                  15

Ala Met Ala Thr Thr Ala Asn Val Pro Pro Ala Asp Lys Tyr Lys Thr
            20                  25                  30

Leu Glu Ala Ala Phe Thr Val Ser Ser Lys Arg Asn Leu Ala Asp Ala
        35                  40                  45
```

```
Val Ser Lys Ala Pro Gln Leu Val Pro Lys Leu Asp Glu Val Tyr Asn
    50                  55                  60

Ala Ala Tyr Asn Ala Ala Asp His Ala Ala Pro Glu Asp Lys Tyr Glu
65                  70                  75                  80

Ala Phe Val Leu His Phe Ser Glu Ala Leu Arg Ile Ile Ala Gly Thr
                85                  90                  95

Pro Glu Val His Ala Val Lys Pro Gly Ala
            100                 105


<210> SEQ ID NO 8
<211> LENGTH: 138
<212> TYPE: PRT
<213> ORGANISM: Phleum pratense

<400> SEQUENCE: 8

Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
            20                  25                  30

Thr Glu Glu Gln Lys Leu Ile Glu Asp Val Asn Ala Ser Phe Arg Ala
        35                  40                  45

Ala Met Ala Thr Thr Ala Asn Val Pro Pro Ala Asp Lys His Lys Thr
    50                  55                  60

Phe Glu Ala Ala Phe Thr Val Ser Ser Lys Arg Asn Leu Ala Asp Ala
65                  70                  75                  80

Val Ser Lys Ala Pro Gln Leu Val Pro Lys Leu Asp Glu Val Tyr Asn
                85                  90                  95

Ala Ala Tyr Asn Ala Ala Asp His Ala Ala Pro Glu Asp Lys Tyr Glu
            100                 105                 110

Ala Phe Val Leu His Phe Ser Glu Ala Leu Arg Ile Ile Ala Gly Thr
        115                 120                 125

Pro Glu Val His Ala Val Lys Pro Gly Ala
    130                 135


<210> SEQ ID NO 9
<211> LENGTH: 132
<212> TYPE: PRT
<213> ORGANISM: Phleum pratense

<400> SEQUENCE: 9

Met Val Ala Met Phe Leu Ala Val Ala Val Val Leu Gly Leu Ala Thr
1               5                   10                  15

Ser Pro Thr Ala Glu Gly Gly Lys Ala Thr Thr Glu Glu Gln Lys Leu
            20                  25                  30

Ile Glu Asp Val Asn Ala Ser Phe Arg Ala Ala Met Ala Thr Thr Ala
        35                  40                  45

Asn Val Pro Pro Ala Asp Lys Tyr Lys Thr Phe Glu Ala Ala Phe Thr
    50                  55                  60

Val Ser Ser Lys Arg Asn Leu Ala Asp Ala Val Ser Lys Ala Pro Gln
65                  70                  75                  80

Leu Val Pro Lys Leu Asp Glu Val Tyr Asn Ala Ala Tyr Asn Ala Ala
                85                  90                  95

Asp His Ala Ala Pro Glu Asp Lys Tyr Glu Ala Phe Val Leu His Phe
            100                 105                 110

Ser Glu Ala Leu Arg Ile Ile Ala Gly Thr Pro Glu Val His Ala Val
        115                 120                 125
```

-continued

```
Lys Pro Gly Ala
    130


<210> SEQ ID NO 10
<211> LENGTH: 138
<212> TYPE: PRT
<213> ORGANISM: Phleum pratense

<400> SEQUENCE: 10

Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
            20                  25                  30

Thr Glu Glu Gln Lys Leu Ile Glu Asp Ile Asn Ala Ser Phe Arg Ala
        35                  40                  45

Ala Met Ala Thr Thr Ala Asn Val Pro Pro Ala Asp Lys Tyr Lys Thr
    50                  55                  60

Phe Glu Ala Ala Phe Thr Val Ser Ser Lys Arg Asn Leu Ala Asp Ala
65                  70                  75                  80

Val Ser Lys Ala Pro Gln Leu Val Pro Lys Leu Asp Glu Val Tyr Asn
                85                  90                  95

Ala Ala Tyr Asn Ala Ala Asp His Ala Ala Pro Glu Asp Lys Tyr Glu
            100                 105                 110

Ala Phe Val Leu His Phe Ser Glu Ala Leu His Ile Ile Ala Gly Thr
        115                 120                 125

Pro Glu Val His Ala Val Lys Pro Gly Ala
    130                 135


<210> SEQ ID NO 11
<211> LENGTH: 120
<212> TYPE: PRT
<213> ORGANISM: Phleum pratense

<400> SEQUENCE: 11

Gly Lys Ala Thr Thr Glu Glu Gln Lys Leu Ile Glu Lys Ile Asn Ala
1               5                   10                  15

Gly Phe Lys Ala Ala Leu Ala Ala Ala Ala Gly Val Gln Pro Ala Asp
            20                  25                  30

Lys Tyr Arg Thr Phe Val Ala Thr Phe Gly Ala Ala Ser Asn Lys Ala
        35                  40                  45

Phe Ala Glu Gly Leu Ser Gly Glu Pro Lys Gly Ala Ala Glu Ser Ser
    50                  55                  60

Ser Lys Ala Ala Leu Thr Ser Lys Leu Asp Ala Ala Tyr Lys Leu Ala
65                  70                  75                  80

Tyr Lys Thr Ala Glu Gly Ala Thr Pro Glu Ala Lys Tyr Asp Ala Tyr
                85                  90                  95

Val Ala Thr Leu Ser Glu Ala Leu Arg Ile Ile Ala Gly Thr Leu Glu
            100                 105                 110

Val His Ala Val Lys Pro Ala Ala
        115                 120


<210> SEQ ID NO 12
<211> LENGTH: 120
<212> TYPE: PRT
<213> ORGANISM: Phleum pratense

<400> SEQUENCE: 12

Gly Lys Ala Thr Thr Glu Glu Gln Lys Leu Ile Glu Lys Ile Asn Asp
```

```
1               5                   10                  15

Gly Phe Lys Ala Ala Leu Ala Ala Ala Ala Gly Val Pro Pro Ala Asp
            20                  25                  30

Lys Tyr Lys Thr Phe Val Ala Thr Phe Gly Ala Ala Ser Asn Lys Ala
        35                  40                  45

Phe Ala Glu Gly Leu Ser Ala Glu Pro Lys Gly Ala Ala Glu Ser Ser
    50                  55                  60

Ser Lys Gly Ala Leu Thr Ser Lys Leu Glu Ala Ala Tyr Lys Leu Ala
65                  70                  75                  80

Tyr Lys Thr Ser Glu Gly Ala Thr Pro Glu Ala Lys Tyr Asp Ala Tyr
                85                  90                  95

Val Ala Thr Leu Ser Glu Ala Leu Arg Ile Ile Ala Gly Thr Leu Glu
            100                 105                 110

Val His Ala Val Lys Pro Ala Ala
        115                 120


<210> SEQ ID NO 13
<211> LENGTH: 120
<212> TYPE: PRT
<213> ORGANISM: Phleum pratense

<400> SEQUENCE: 13

Gly Lys Ala Thr Thr Glu Glu Gln Lys Leu Ile Glu Lys Ile Asn Ala
1               5                   10                  15

Gly Phe Lys Ala Ala Leu Ala Ala Ala Ala Gly Val Pro Pro Ala Asp
            20                  25                  30

Lys Tyr Arg Thr Phe Val Ala Thr Phe Gly Ala Ala Ser Asn Lys Ala
        35                  40                  45

Phe Ala Glu Gly Leu Ser Gly Glu Pro Lys Gly Ala Ala Glu Ser Ser
    50                  55                  60

Ser Lys Ala Ala Leu Thr Ser Lys Leu Asp Ala Ala Tyr Lys Leu Ala
65                  70                  75                  80

Tyr Lys Thr Ala Glu Gly Ala Thr Pro Glu Ala Lys Tyr Asp Ala Tyr
                85                  90                  95

Val Ala Thr Leu Ser Glu Ala Leu Arg Ile Ile Ala Gly Thr Leu Glu
            100                 105                 110

Val His Ala Val Lys Pro Ala Ala
        115                 120


<210> SEQ ID NO 14
<211> LENGTH: 106
<212> TYPE: PRT
<213> ORGANISM: Phleum pratense

<400> SEQUENCE: 14

Gly Lys Ala Thr Thr Glu Glu Gln Lys Leu Ile Glu Asp Ile Asn Val
1               5                   10                  15

Gly Phe Lys Ala Ala Val Ala Ala Ala Ala Ser Val Pro Ala Ala Asp
            20                  25                  30

Lys Phe Lys Thr Phe Glu Ala Ala Phe Thr Ser Ser Ser Lys Ala Ala
        35                  40                  45

Ala Ala Lys Ala Pro Gly Leu Val Pro Lys Leu Asp Ala Ala Tyr Ser
    50                  55                  60

Val Ala Tyr Lys Ala Ala Val Gly Ala Thr Pro Glu Ala Lys Phe Asp
65                  70                  75                  80

Ser Phe Val Ala Ser Leu Thr Glu Ala Leu Arg Val Ile Ala Gly Ala
```

-continued

```
            85                  90                  95

Leu Glu Val His Ala Val Lys Pro Val Thr
            100                 105
```

VARIANTS OF GROUP 6 ALLERGENS OF THE TRUE GRASSES HAVING REDUCED ALLERGENEITY DUE TO MUTAGENESIS OF PROLINE RESIDUES

SEQUENCE LISTING

The instant application contains a Sequence Listing which has been submitted in ASCII format via EFS-Web and is hereby incorporated by reference in its entirety. Said ASCII copy, created on Apr. 26, 2013, is named MERCK-3975_SL.txt and is 12,967 bytes in size.

AREA OF THE INVENTION

The present invention relates to the preparation and use of recombinant variants of group 5 allergens of the Poaceae (true grasses), which are characterised by reduced IgE reactivity compared with known wild-type allergens and at the same time substantially retained reactivity with T-lymphocytes.

These hypoallergenic allergen variants can be employed for specific immunotherapy (hyposensitisation) of patients having grass pollen allergy or for the preventative treatment for preventing the development of grass pollen allergies.

A preferred embodiment of the invention relates to variants of the allergen Phl p 6 of Timothy grass (*Phleum pratense*) in which the prolines in positions 29, 30, 57, 79 have mutated singly or in combinations.

BACKGROUND OF THE INVENTION

Type 1 allergies have worldwide importance. Up to 20% of the population in industrialised countries suffer from complaints such as allergic rhinitis, conjunctivitis or bronchial asthma.

These allergies are caused by sources of various origin, such as trees and grasses (pollen), fungi (spores), mites (excrement), cats or dogs. The allergen sources are released directly into the air (pollen, spores) or can reach the air bonded to diesel soot particles (pollen) or house dust (mite excrement, skin particles, hair). Since the allergy-triggering substances are located in the air, the term aeroallergens is also used.

The type 1 allergy-triggering substances are proteins, glycoproteins or polypeptides. After uptake via mucous membranes, these allergens react with the IgE molecules bound to the surface of mast cells in sensitised persons. If these IgE molecules are crosslinked with one another by an allergen, this results in the secretion of mediators (for example histamine, prostaglandins) and cytokines by the effector cell and thus in the corresponding allergic symptoms.

Up to 40% of type 1 allergy sufferers exhibit specific IgE reactivity with pollen extracts of true grasses (Burney et al., 1997, J. Allergy Clin. Immunol. 99:314-322; D'Amato et al., 1998, Allergy 53: 567-578; Freidhoff et al., 1986, J. Allergy Clin Immunology, 78, 1190-2002). The family of the true grasses (Poaceae) encompasses more than 10000 species, many more than 20 of which are hitherto known as triggers of allergic symptoms (Andersson & Lidholm, 2003, Int. Arch. Allergy Immunol. 130:87-107; Esch, 2008, Allergens and Allergen Immunotherapy, Clinical Allergy and Immunology Series, 107-126).

Most of the allergy-triggering true grasses belong to the Pooideae sub-family. Besides the grass species occurring as wild forms, such as, for example, *Holcus lanatus* (velvet grass), *Phalaris aquatica* (canary grass), *Anthoxanthum odoratum* (sweet vernal grass), *Dactylis glomerata* (orchard grass), *Festuca pratensis* (meadow fescue), *Poa pratensis* (Kentucky blue grass) or *Lolium perenne* (rye grass), cultivated cereals, such as *Triticum aestivum* (wheat), *Secale cereale* (rye) and *Hordeum vulgare* (barley), are also known members of this sub-family.

One of the Pooideae species which has been investigated best with respect to its allergens is Timothy grass (*Phleum pratense*), which is widespread worldwide as a wild plant and also plays a commercial role as a pasture plant and hardy feed grass.

Depending on the relative frequency in a population with which the individual allergen molecules react with the IgE antibodies of allergy sufferers, a distinction is made between major and minor allergens.

Six allergens of Timothy grass can be regarded as major allergens: Phl p 1 (Petersen et al., 1993, J. Allergy Clin. Immunol. 92: 789-796), Phl p 5 (Matthiesen and Löwenstein, 1991, Clin. Exp. Allergy 21: 297-307; Petersen et al., 1992, Int. Arch. Allergy Immunol. 98: 105-109), Phl p 6 (Petersen et al., 1995, Int. Arch. Allergy Immunol. 108, 49-54), Phl p 2/3 (Dolecek et al., 1993, FEBS 335 (3): 299-304), Phl p 4 (Haavik et al., 1985, Int. Arch. Allergy Appl. Immunol. 78: 260-268; Valenta et al., 1992, Int. Arch. Allergy Immunol. 97: 287-294; Nandy et al., Biochem. Biophys. Res. Commun., 2005, 337(2): 563-70) and Phl p 13 (Suck et al., 2000, Clin. Exp. Allergy 30: 1395-1402).

The first description of Phl p 6 came as early as 1978. A protein fraction purified from Timothy grass pollen, which was called "Ag19", contained an allergen with a size of about 15 kDa, which was later classified in the official allergen nomenclature and was continued as Phl p 6 (Løwenstein, 1978, Allergy 33: 30-41; WHO/IUIS Allergen Nomenclature Subcommittee, www.allergen.org). Phl p 6 is classified as a major allergen since Phl p 6-reactive IgE antibodies can be detected in about 70% of grass pollen allergy sufferers. (Rossi et al., 2001, Allergy, 56: 1180-85; Vrtala et al., 1999, J. Immunol. 15; 163:5489-9).

Physicochemical investigations of the allergen from grass pollen extract detected two protein variants which differ in their primary sequence (Blume et al., 2004, Proteomics 4: 1366-71). These isoforms are attributed to two cDNA sequences identified in expression libraries of Timothy grass pollen and carry the WHO/IUIS names Phl p 6.0101 (GenBank: Z27082.1; UniProt: P43215; see FIGS. 15 and 16 or SEQ ID NO:3 and SEQ ID NO: 4, with propeptide see FIG. 19 or SEQ ID NO:9; Petersen et al., 1995, Int. Arch. Allergy Immunol. 108: 55-59) and Phl p 6.0102 (GenBank: Y16955; UniProt: 065868; see FIGS. 3 and 4 or SEQ ID NO:1 and SEQ ID NO: 2, with propeptide see FIG. 20 or SEQ ID NO:10; Vrtala et al., 1999, J. Immunol. 15; 163:5489-9). Apart from a signal peptide, the proteins each consist of 110 amino acids and differ at only two positions (Val 14→Ile and Arg→95 His, starting from ripe Phl p 6.0101), which cause a difference in the molecular weight of 5 Da (11790 Da of Phl p 6.0101 compared with 11785 Da of Phl p 6.0102; FIG. 1).

The pollen of other true grass species of the Poaceae family and in particular the Pooideae sub-family may contain major allergens which are homologous with the allergens of Timothy grass. Such allergens which occur across species are summarised as an allergen group. The high structural homology of such related allergens, which is ultimately based on a similar amino acid sequence, causes correspondingly high cross-reactivity of the molecules with IgE antibodies (Lorenz et al., 2009, Int. Arch. Immunol. 148:1-17). It is also known that atopic persons who react allergically to major allergens of Timothy grass may have been primarily sensitised by one of the other related species of the true grasses. Finally, this cross-reactivity may mean that sensitization by one grass species is sufficient to trigger an allergic reaction by other related grasses.

A group 6 allergen which is cross-reactive with Phl p 6 has already been detected at the protein level in pollen of Kentucky blue grass (*Poa pratensis*) (Vrtala et al., 1999, J. Immunol. 15; 163:5489-9; Niederberger et al., 1998, J. Allergy Clin. Immunol. 101 (2): 258-264).

Besides the cross-reactivity of the group 6 allergens with one another, cross-reactivity with major allergens from group 5 is also known. The polypeptide chain of Phl p 6 exhibits great similarity with an N-terminal region of Phl p 5, which has a size of about 26-28 kDa (FIG. 1, FIG. 2). It is thought that the allergens can be attributed to a common original gene (Petersen et al., 1995, Int. Arch. Allergy Immunol. 108: 55-59). Both proteins form α-helical secondary structures, but no β-folded sheet structures. X-ray structural analysis has shown that the four α-helices of Phl p 6 fold to form a characteristic helix bundle (RCSB Protein Data Bank entry: 1NLX; Fedorov et al., 2003; FIG. 1), a structure which has also been detected in fragments of Phl p 5 (Rajashankar et al., 2002, Acta Cryst. D58:1175-1181; Maglio et al., 2002, Protein Engineering 15: 635-642; Wald et al., 2007, Clin. Exp. Allergy 37:441-450). The similarity between the allergens has the effect that some of the Phl p 5-reactive IgE antibodies also bind to Phl p 6 (Petersen et al., 1995, Int. Arch. Allergy Immunol. 108: 49-54; Andersson & Lidholm, 2003, Int. Arch. Allergy Immunol. 130:87-107).

Specific immunotherapy (SIT) or hyposensitisation is regarded as an effective approach to the therapeutic treatment of allergies (Fiebig 1995 Allergo J. 4 (6):336-339, Bousquet et al., 1998, J. Allergy Clin. Immunol. 102 (4): 558-562; Cox et al., 2007, J. Allergy Clin. Immunol. 120:S25-85; James & Durham, 2008, Clin. Exp. Allergy 38: 1074-1088).

The classical therapy form of injection therapy (SLIT), in which natural allergen extracts are injected subcutaneously into the patient in increasing doses, has been used successfully for about 100 years. In this therapy, the immune system of the allergy sufferer is repeatedly confronted with allergens, causing reprogramming of the immune system to be achieved together with tolerance of the allergens. After uptake of the antigens from the allergen preparations by antigen-presenting cells, peptides are presented to the antigens on the cell surface. Some particular peptides which contain so-called T-cell epitopes are recognised by antigen-specific T-cells. This binding results, inter alia, in the development of various types of T-cells having a regulatory function. In the course of SIT, the regulatory T-cell response results in tolerance of the allergen, the downregulation of $T_H2$ cytokines, the restoration of the $T_H1/T_H2$ equilibrium, the suppression of allergen-specific IgE, the induction of IgG4, IgG1 and IgA antibodies, the suppression of effector cells (mast cells, basophils and eosinophils) and the renewal of inflamed tissue (Akdis et al., 2007, J. Allergy Clin. Immunol. 119 (4):780-789; Larche et al., 2008, Nature Reviews 6:761-771). The T-cell epitopes are thus of crucial importance for the therapeutic action of allergen preparations in the case of hyposensitisation.

Owing to the cross-reactivity of the major allergens of the true grasses which is present at IgE and also at T-cell level, successful therapy with an allergen extract of a single representative grass species is usually sufficient (Mailing et al., 1993, EAACI Position Paper: Immunotherapy, Allergy 48: 9-35; Cox et al., 2007, J Allergy Clin Immunol 120: 25-85).

Besides subcutaneous immunotherapy, a sublingual therapy form, in which the allergens or allergen derivatives are taken up via the oral mucous membrane, is undergoing clinical trials and use as an alternative to injection therapy (James & Durham, 2008, Clin. Exp. Allergy 38: 1074-1088).

A further possibility is treatment with expressible DNA which encodes for the relevant allergens (immunotherapeutic vaccination). Experimental evidence of the allergen-specific influencing of the immune response has been furnished in rodents by injection of allergen-encoding DNA (Hsu et al. 1996, Nature Medicine 2 (5):540-544, Weiss et al., 2006, Int. Arch. Allergy Immunol. 139: 332-345).

In all these therapy forms, there is a fundamental risk of allergic reactions or even anaphylactic shock (Kleine-Tebbe, 2006, Allergologie, 4:135-156). In order to minimise these risks, innovative preparations in the form of allergoids are employed. These are chemically modified allergen extracts which have significantly reduced IgE reactivity, but identical T-cell reactivity compared with the untreated extract (Fiebig 1995 Allergo J. 4 (6):336-339, Kahlert et al., 1999, Int. Arch. Allergy Immunol, 120: 146-157).

Therapy optimisation is possible with allergens prepared by recombinant methods. Defined cocktails of high-purity allergens prepared by recombinant methods, which are optionally matched to the individual sensitisation patterns of the patients, could replace extracts from natural allergen sources, since, apart from the various allergens, the latter contain a relatively large number of immunogenic, but non-allergenic accompanying proteins. Initial clinical studies with recombinant allergens have already been carried out with success (Jutel et al., 2005, J. Allergy Clin. Immunol., 116: 608-613; Valenta & Niederberger, 2007, J. Allergy Clin. Immunol. 119: 826-830).

Realistic prospects which may result in safe hyposensitisation with recombinant expression products are offered specifically by mutated recombinant allergens in which IgE epitopes are modified without impairing the T-cell epitopes which are essential for the therapy (Schramm et al. 1999, J. Immunol. 162:2406-2414). These hypoallergenic proteins could be employed in relatively high doses during SIT without increasing the probability of undesired IgE-promoted side effects.

In the past, such "hypoallergenic" variants with reduced IgE binding have been published for many aeroallergens (inter alia pollen and house dust mite allergens) and food allergens. On the basis of the DNA of unmodified allergens, it has been possible to prepare and express a recombinant DNA, inter alia by fragmentation, oligomerisation, deletions, point mutations or recombination of individual sections of an allergen (DNA shuffling) (Ferreira et al., 2006, Inflamm. & Allergy—Drug Targets 5: 5-14; Bhalla & Singh, 2008, Trends in Biotechnology 26:153-161; Westritschnig et al., 2007, J. Immunol. 179: 7624-7634).

Regarding the group 6 allergens of the grasses, only a single mutation strategy has been published to date, in which the first ninety nucleotides, encoding for amino acids 1-30 of ripe Phl p 6, have been deleted. The molecule was expressed as histidine fusion molecule, purified and investigated with respect to its immunological properties. The N-terminal deletion resulted in reduced IgE binding and reduced ability to be stimulated by basophilic granulocytes (Vrtala et al., 2007, J. Immunol. 179: 1730-1739). In a later paper, the same molecule was connected to a recombinant variant of Phl p 2 to give a hybrid molecule (Linhart et al., 2008, Biol. Chem. 389: 925-933). A mutation strategy based on point mutations, as described for other allergens, has not yet been published hitherto for group 6 grass pollen allergens.

The object on which the present invention is based consisted in the provision of novel variants of group 6 allergens of the Poaceae at the protein and DNA level which are distinguished by reduced IgE reactivity at the same time as substantial retention of the T-cell reactivity and are therefore suitable for curative and preventive specific immunotherapy and immunotherapeutic DNA vaccination.

DESCRIPTION OF THE INVENTION

Surprisingly, it has been found that variants of group 6 allergens of the true grass family (Poaceae) in which the prolines which correspond in an alignment to the prolines in positions 29, 30, 57, 79 in the amino acid sequence of wild-type Phl p 6 have mutated singly or in combinations, have reduced IgE reactivity compared with the wild-type allergens and at the same time have substantially retained reactivity with T-lymphocytes and are thus hypoallergenic.

The invention accordingly relates to hypoallergenic variants of group 6 allergens of the true grass family (Poaceae) in which the prolines which correspond in an alignment to the prolines in positions 29, 30, 57, 79 in the amino acid sequence of wild-type Phl p 6 have mutated singly or in combinations.

Particular preference is given to allergen variants according to the invention, characterised in that the prolines have been deleted or substituted.

Preference is given to hypoallergenic variants according to the invention of group 6 allergens from the Pooideae subfamily, preferably from the groups Poodae and Triticodae, preferably represented by *Phleum pratense, Holcus lanatus, Phalaris aquatica, Anthoxanthum odoratum, Dactylis glomerata, Lolium perenne, Poa pratensis, Festuca pratensis, Hordeum vulgare, Secale cereale* and *Triticum aestivum*. They are preferably hypoallergenic variants according to the invention of Tri a 6, Sec c 6 and Hor v 6 from *Triticum aestivum, Secale cereale* and *Hordeum vulgare*. Particular preference is given to hypoallergenic variants according to the invention of group 6 allergens of the Poodae. These group 6 allergens are preferably Phl p 6, Poa p 6, Hol p 6, Lol p 6 and Pha a 6 from *Phleum pratense, Lolium perenne, Poa pratensis, Holcus lanatus* and *Phalaris aquatica* and very particularly preferably Poa p 6 and Phl p 6, in particular Phl p 6. All naturally occurring isomers, polymorphs and variants of the above-mentioned allergens, and precursor proteins thereof, are also in accordance with the invention.

In the hypoallergenic variants according to the invention, the mutated prolines are preferably those which correspond in an alignment to the prolines in positions 29, 30, 57, 79 in the amino acid sequence of ripe Phl p 6.0101 or variants thereof (SEQ ID NO:4, SEQ ID NO:7, SEQ ID NO:8) or of ripe Phl p 6.0102 (SEQ ID NO:2), particularly preferably of ripe Phl p 6.0102.

Although it was known that prolines can exert an influence on the protein structure, specific point mutations of proline residues as starting point for the generation of hypoallergenic mutants of allergens were merely investigated for the group 2 principal allergen of the house dust mite *Dermatophaogides farinae* (Der f 2, replacement of proline residues by alanine) (Takai et al., 2000, Eur. J. Biochem. 267: 6650-6656). However, the IgE binding ability and ability to stimulate basophilic cells was only slightly reduced in the case of three point mutants, while the other three behaved like the unmodified allergen. The proline mutations in the case of Der f 2 thus exhibited an only very weak reduction in allergeneity, or none at all. Further strategies for the preparation of hypoallergenic mutants by proline exchange mutations have not been published. Thus, the person skilled in the art would not have expected proline mutations to be successful as starting point for the generation of hypoallergenic mutants of allergens.

In addition, it has hitherto not been investigated for any allergen how a specific deletion of proline residues affects the entire IgE binding ability of the expression product and what effects occur on the activation of allergy-relevant effector cells.

The amino acid sequences of Phl p 6 or of the two isoforms (Phl p 6.0101, GenBank: Z27082.1, UniProt: P43215; Phl p 6.0102, GenBank: Y16955, UniProt: O65868) have 7 proline residues (FIG. 1). The prolines in amino acid positions 29, 30, 57, 79 and 101 are located directly at the beginning or end of α-helices or are involved in the formation of the protein surface (FIG. 2). The proline residue at position 61 is part of the third helix, while proline 108 is localised close to the C terminal.

Starting from the amino acid sequences of the Phl p 6 isoforms Phl p 6.0101 (SEQ ID NO:4) and Phl p 6.0102 (SEQ ID NO 2), the recombinant unmodified wild-type allergen (rPhl p 6 wt; FIG. 4) and the variants according to the invention modified by genetic engineering are prepared. Analogously to the preparation process described below, the wild-type proteins and the hypoallergenic variants according to the invention of the other group 6 allergens according to the invention of the true grasses, for example Poa p 6, can also be prepared. To this end, the prolines which correspond in an alignment to the prolines in positions in positions 29, 30, 57, 79 in the amino acid sequence of wild-type Phl p 6 have mutated singly or in combinations, preferably by substitution or deletion.

The allergen variants according to the invention should be prepared starting from the cloned DNA sequence with the aid of genetic engineering methods. Preparation processes according to the invention are known to the person skilled in the art from relevant laboratory procedures and publications, such as, for example: E. F. Fritsch, J. Sambrook, T. Maniatis, Molecular Cloning, Cold Spring Harbor Laboratory Press, 1989.

In addition to the variations described of group 6 allergens, further modifications at other positions—for example in order to increase the hypoallergeneity—are naturally also possible. These modifications can be, for example, amino acid insertions, deletions, replacements and cleavages of the protein into fragments and fusions of the protein or fragments thereof with other proteins or peptides, and multimers through fusions of identical proteins or fragments.

Fragments according to the invention preferably comprise 20-109 amino acids, preferably 30-100 amino acids, particularly preferably 40-90 amino acids. Variants according to the invention additionally include precursor proteins, such as, for example, ProPhl p 6, with a prior natural or artificial signal sequence, as depicted, for example, in FIGS. 18, 19 and 20 (SEQ ID NO: 8, SEQ ID NO: 9, SEQ ID NO: 10). Also in accordance with the invention are fusion proteins having N- or C-terminal fusion tags (for example His tag, as in FIGS. 5 and 6, MBP tag, expression control sequences, etc.), hybrid molecules, such as, for example, fusions with other allergens or hypoallergenic variants thereof or fusions of fragments in any desired sequence. In addition, the variants according to the invention also comprise homologous sequences (polymorphs (SNPs), isoforms) having an identity of the amino acid sequence of at least 80% with the relevant group 6 wild-type allergen, preferably of at least 90% with the relevant group 6 wild-type allergen, particularly preferably of at least 95% with the relevant group 6 wild-type allergen. In these variants, one or a few amino acids are preferably replaced conservatively, for example a polar amino acid is substituted by another polar amino acid or a neutral amino acid is substituted by another neutral amino acid, but variants due to non-conservative replacement are also in accordance with the invention. Multimers preferably include dimers or trimers of the hypoallergenic variants according to the invention connected by a linker sequence or subjected to direct fusion.

Examples of such variants are the variants of Phl p 6.0101 as shown in FIGS. 17 and 18 (SEQ ID NO:7, SEQ ID NO: 8)—in which individual amino acids which are not relevant for the action according to the invention have been replaced, or are lacking three amino acids at the N terminal, or precursor sequences thereof having signal peptides at the N terminal, and the like. Further examples of variants according to the invention are polymorphic variants, such as, for example, the two isomers Phl p 6.0101 and Phl p 6.0102 themselves, and further variants with replacement of one or more amino acids, omission of one or more amino acids at the N- and/or C-terminal or with corresponding deletion gaps within the amino acid sequence. Likewise in accordance with the invention are variants with insertions of single or multiple amino acids individually at various positions or as a group at a position within the amino acid sequence or at the N and/or C terminal.

The invention thus also relates to hypoallergenic variants of group 6 allergens of the true grasses (Poaceae), characterised in that it is a fragment or a variant of a hypoallergenic variant according to the invention, or a multimer of one or more hypoallergenic variants according to the invention or characterised in that one or more hypoallergenic variants according to the invention or fragments, variants or multimers thereof are a constituent of a recombinant fusion protein.

In addition, the invention relates to a DNA molecule which encodes for a hypoallergenic variant according to the invention.

The invention furthermore relates to a recombinant expression vector containing a DNA molecule according to the invention of this type functionally connected to an expression control sequence. An expression control sequence is taken to mean, for example, a promoter or a sequence section with the aid of which the expression of the target protein is influenced and which is functionally connected to the target gene, but does not necessarily have to be localised in the direct vicinity of the target gene.

The invention also relates to a non-human host organism transformed by means of a DNA molecule according to the invention or an expression vector according to the invention.

The invention relates to a process for the preparation of a hypoallergenic variant according to the invention by cultivation of a non-human host organism according to the invention and isolation of the corresponding allergen variant from the culture.

Suitable non-human host organisms can be pro- or eukaryotic, single- or multicelled organisms, such as bacteria or yeasts. A host organism which is preferred in accordance with the invention is *E. coli.*

The influence of the deletion of single or of two closely adjacent prolines on the IgE binding ability of Phl p 6 can be investigated by deletion of prolines 29+30 of proline 57, of proline 79 and of proline 101. In the Phl p 6 wild-type protein, these prolines are localised in the loop regions at the beginning or end of α-helices (FIG. 1; FIG. 2). Proline 61 and proline 108 are preferably not modified, since corresponding variants exhibit no significant efficacy. The influence of proline mutations in the corresponding homologous positions of the other group 6 allergens according to the invention of the true grasses, for example Poa p 6, on the IgE binding ability can be investigated analogously.

For faster from high-yield purification, the encoding DNA for these investigations is provided with a sequence encoding for an N-terminal hexahistidine fusion component (+6His) (FIG. 5, SEQ ID NO:5; FIG. 6, SEQ ID NO:6). The tag-free variants according to the invention and wild-type proteins which can be employed for pharmaceutical purposes are likewise purified by standard methods and confirm the results of the His-tag proteins.

Sequences encoding for proteins rPhl p 6 d[P29, 30]+6His, rPhl p 6 d[P57]+6His, rPhl p 6 d[P79]+6His and rPhl p 6 d[P101]+6His, for example, are prepared correspondingly. The sequences can be expressed in all known eukaryotic and prokaryotic expression systems, preferably in *E. coli.* The proteins are subsequently purified as soluble monomers by standard methods. Finally, purity can be checked by analysis in a denaturing polyacrylamide gel (SDS-PAGE) (FIG. 7).

Analytical gel filtration (SEC) with coupling of a refractometer (RI detector) and a multiangle light-scattering detector (MALS detector) allows online determination of the molecular weight of the eluted proteins (SEC/MALS/RI method).

Thus, the analysis of rPhl p 6 d[P29, 30]+6His, rPhl p 6 d[P57]+6His, rPhl p 6 d[P79]+6His and rPhl p 6 d[P101]+6His by SEC/MALS/RI shows that these variants according to the invention are in the form of pure monomers in solution (FIG. 8, Table 1).

The IgE binding ability of the recombinant variants according to the invention can be determined by a method in which the proteins are immobilised on a nitrocellulose membrane and confronted with IgE antibodies of individual sera of clinically defined grass pollen allergy sufferers (strip test). The allergen variants/antibody complexes are subsequently coloured by enzymatic reaction (FIG. 9).

In this method, mutant rPhl p 6 d[P101]+6His exhibits similarly good IgE binding as the unmodified allergen with all sera tested (FIG. 9). It follows from this that deletion of proline 101 has no significant influence on the IgE binding ability of Phl p 6. The IgE binding of mutants rPhl p 6 d[P29, 30]+6His, rPhl p 6 d[P57]+6His and rPhl p 6 d[P79]+6His is different in the sera of different grass pollen allergy sufferers. This is due to variations in the composition of the IgE population of individual allergy sufferers with respect to affinity and epitope specificity of the IgE antibodies. Mutants rPhl p 6 d[P57]+6His and rPhl p 6 d[P79]+6His exhibit significantly reduced IgE reactivity with most sera compared with unmodified rPhl p 6 wt+6H is. However, the lowest IgE binding is observed throughout in the case of mutant rPhl p 6 d[P29, 30]+6His (FIG. 9).

The recombinant variants according to the invention can, in addition, be investigated with respect to their binding ability to human IgE antibodies by IgE inhibition tests (EAST). In this method, the allergen/IgE interaction can be investigated in solution, which enables interfering masking of epitopes of the test substance, for example due to immobilisation on a membrane, to be excluded.

In the present example, two sera of grass pollen allergy sufferers are selected which differed significantly in the strip test method through their IgE binding to mutant rPhl p 6 d[P29, 30]+6H is. Serum P32 represents the group of sera which exhibit still detectable IgE binding to rPhl p 6 d[P29, 30]+6His in the strip test (group "A"), while serum P82 is selected as representative of the group of sera (group "B") having no longer detectable reactivity (FIG. 9, FIG. 14).

Using this test method, the reduced IgE binding ability of mutants rPhl p 6 d[P29, 30]+6His, rPhl p 6 d[P57]+6His and rPhl p 6 d[P79]+6His compared with unmodified rPhl p 6 wt+6His can be confirmed, in agreement with the results of the strip test (FIG. 10).

The results of the strip test method are thus not attributable to partial masking of IgE epitopes, but instead reflect the reduced IgE binding ability of dissolved proteins correctly.

Mutant rPhl p 6 d[P101]+6His exhibits an IgE binding ability which corresponds to that of the wild-type allergen using serum P32 in the entire concentration range (FIG. 10). On use of serum P82, lower IgE binding is only observed at low protein concentrations, while the IgE binding again corresponds to that of the wild-type allergen at high concentrations (FIG. 10).

A reduction of the IgE binding ability of Phl p 6 is thus in principle also possible by deletion of proline residue 101, but this effect is apparently so small that it cannot be detected in the strip test method at all and only at low concentrations by the IgE inhibition test (FIG. 9, FIG. 10).

The reduced IgE binding ability of mutants rPhl p 6 d[P29, 30]+6His, rPhl p 6 d[P57]+6His and rPhl p 6 d[P79]+6His is, by contrast, easily detectable in the strip test method with the majority of allergy sufferer sera and is given throughout the concentration range investigated in the IgE inhibition tests (FIG. 9, FIG. 10).

This basically proves that the deletion of proline residues from group 6 allergens can reduce the IgE binding ability. On the other hand, only the deletion of certain prolines results in relevantly reduced IgE binding.

By means of a test with basophilic granulocytes of a clinically defined grass pollen allergy sufferer, the effect of the reduced IgE binding ability of the variants according to the invention on the activation of human effector cells can be investigated in vitro.

The granulocytes employed in the test are isolated from the whole blood of an allergy sufferer, in the present example allergy sufferer P21. This allergy sufferer represents those allergy sufferers whose IgE antibodies exhibit detectable binding to rPhl p 6 d[P29, 30]+6His in the strip test method (group "A"; FIG. 9, 14).

At the same concentration of the recombinant wild-type allergen and of variants rPhl p 6 d[P29, 30]+6His, rPhl p 6 d[P57]+6His, and Phl p 6 d[P79]+6His rPhl p 6 d[P29, 30]+6His according to the invention, the variants according to the invention exhibit lower binding to membrane-bound IgE antibodies and consequently drastically reduced activation of basophilic granulocytes (FIG. 11).

The results thus confirm functionally reduced allergeneity of mutants rPhl p 6 d[P29, 30]+6His, rPhl p 6 d[P57]+6His and rPhl p 6 d[P79]+6H is. It can thus be confirmed with this test that proline mutations in these two regions of Phl p 6 also reduces the IgE binding ability, at least in some allergy sufferers.

The present invention therefore furthermore relates to hypoallergenic variants of group 6 allergens of the true grass family (Poaceae) in which the prolines which correspond in an alignment to the prolines in positions 29, 30, 57, 79 in the amino acid sequence of wild-type Phl p 6 have mutated singly.

The present invention preferably relates to hypoallergenic variants of Phl p 6 or Poa p 6 in which the prolines which correspond in an alignment to the prolines in positions 29, 30, 57, 79 in the amino acid sequence of wild-type Phl p 6 have mutated singly.

The present invention particularly preferably relates to hypoallergenic variants of Phl p 6 in which the prolines which correspond in an alignment to the prolines in positions 29, 30, 57, 79 in the amino acid sequence of wild-type Phl p 6 have mutated singly.

Particular preference is therefore given to hypoallergenic variants of group 6 allergens of the true grass family (Poaceae) in which the prolines which correspond in an alignment to the prolines in positions 29, 30, 57, 79 in the amino acid sequence of ripe Phl p 6.0102 (SEQ ID NO:2) have mutated been removed singly.

The present invention furthermore preferably relates to hypoallergenic variants according to the invention of group 6 allergens of the true grass family (Poaceae) in which the prolines which correspond in an alignment to the prolines in positions 29, 30, 57, 79 in the amino acid sequence of wild-type Phl p 6 have been removed singly.

In addition, the present invention furthermore relates to hypoallergenic variants according to the invention of group 6 allergens of the true grass family (Poaceae) in which the prolines which correspond in an alignment to the prolines in positions 29, 30, 57, 79 in the amino acid sequence of wild-type Phl p 6 have been substituted individually. Here, proline is replaced by way of example by leucine (L). In accordance with the invention, however, the prolines according to the invention can be replaced by any amino acid.

In particular, the hypoallergenic variants rPhl p 6 d[P29], rPhl p 6 d[P30], rPhl p 6 d[P29, 30], rPhl p 6 d[P57], rPhl p 6 d[P79], rPhl p 6 P29L, rPhl p 6 P30L. rPhl p 6 P29L, P30L, rPhl p 6 P57L and rPhl p 6 P79L, and the like, including all hypoallergenic variants according to the invention described below, are in accordance with the invention, where the numbering follows the sequence of Phl p 6, in particular of ripe Phl p 6.0102.

Furthermore, these examples are not restricted to variants of Phl p 6, but also relate, in particular, to Poa p 6 and the group 6 allergens of all other true grasses.

In addition, the still detectable IgE binding ability of the hypoallergenic variants according to the invention of group 6 allergens can be reduced further by combination of proline mutations. Thus, owing to the greatly reduced IgE binding of mutant rPhl p 6 d[P29, 30]+6His and the fact that the IgE binding ability can also be partially reduced by the deletion of prolines 57 and 79, nucleic acids are produced which contain the mutations in combinations. Based on the DNA of mutant rPhl p 6 d[P29, 30]+6His, the prolines in positions 57 and 79 are either deleted or converted into the amino acid leucine.

Accordingly, sequences encoding for proteins rPhl p 6 d[P29, 30, 57]+6His and rPhl p 6 d[P29, 30, 79]+6His as well as rPhl p 6 d[P29, 30] P57L+6His and rPhl p 6 d[P29, 30] P79L+6His are prepared. These variants encode for proteins which carry proline mutations in two of the loops which connect the α-helices of Phl p 6 (FIG. 2).

In addition, a nucleic acid encoding for rPhl p 6 d[P29, 30] P57L P79L+6His are prepared in order to produce an allergen variant which has proline mutations in three loop regions (FIG. 2). As already mentioned above, the sequences are preferably expressed in *E. coli*, and the proteins are purified by standard methods.

The purity is likewise investigated by SDS-PAGE and by SEC/MALS/RI (FIG. 12, FIG. 13). All proteins according to the invention can thus be prepared in high purity and solubility.

The SEC/MALS/RI method reveals significant differences for above-mentioned mutants with respect to the property of forming dimers (FIG. 13, Table 2). The molecular weights determined for proteins rPhl p 6 d[P29, 30, 57]+6His, rPhl p 6 d[P29, 30] P57L+6His and rPhl p 6 d[P29, 30] P57L P79L+6His exhibit a clear tendency towards the formation of dimers. Proteins rPhl p 6 d[P29, 30, 79]+6His and rPhl p 6 d[P29, 30] P79L+6His are only detected in the monomeric form (Table 2). It can be concluded from this result that the modification of the position proline 57, but not proline 79, modifies rPhl p 6 d[P29, 30] in such a way that a dimerisation tendency is induced.

The determination of the IgE binding ability by the strip test method surprisingly shows in fact that the sera of allergy sufferers from group "A" which have detectable IgE binding to rPhl p 6 d[P29, 30] have significantly reduced IgE binding to the optimised variants (FIG. 14). Whether prolines 57 and 79 have been deleted or replaced by another amino acid apparently has just as little influence on the reduction of the IgE binding ability as the ability to form dimers. It is thus shown that a simultaneously present modification of a plurality of amino acid residues from the group of prolines 29, 30, 57 and 79 significantly reduces the IgE binding further.

The present invention therefore furthermore relates to hypoallergenic variants of group 6 allergens of the true grass family (Poaceae) in which the prolines which correspond in an alignment to the prolines in positions 29, 30, 57, 79 in the amino acid sequence of wild-type Phl p 6 have mutated in combinations. Preference is given to mutations through deletion and through substitution by other amino acids. Any amino acid can be selected here for replacement by proline.

The present invention preferably relates to hypoallergenic variants of Phl p 6 or Poa p 6 which the prolines which correspond in an alignment to the prolines in positions 29, 30, 57, 79 in the amino acid sequence of wild-type Phl p 6 have mutated in combinations.

The present invention particularly preferably relates to hypoallergenic variants of Phl p 6 in which the prolines which correspond in an alignment to the prolines in positions 29, 30, 57, 79 in the amino acid sequence of wild-type Phl p 6 have mutated in combinations.

Particular preference is given to hypoallergenic variants of group 6 allergens of the true grass family (Poaceae) in which the prolines which correspond in an alignment to the prolines in positions 29, 30, 57, 79 in the amino acid sequence of ripe Phl p 6.0102 (SEQ ID NO:2) have mutated in combinations.

Particular preference is given to hypoallergenic variants according to the invention in which prolines 29, 30, 57, 79 have been removed in combinations. Particular preference is also given to hypoallergenic variants according to the invention in which prolines 29, 30, 57, 79 have been substituted in combinations.

In addition, particular preference is given to hypoallergenic variants according to the invention in which prolines 29, 30, 57, 79 have been removed and/or substituted in combinations. In particular, hypoallergenic variants rPhl p 6 d[P29, 30, 57], rPhl p 6 d[29, 30, 79], rPhl p 6 d[29, 30, 57, 79], rPhl p 6 d[P29, 57], rPhl p 6 d[P30, 57], rPhl p 6 d[29, 79], rPhl p 6 d[30, 79], rPhl p 6 d[29, 57, 79], rPhl p 6 d[30, 57, 79], rPhl p 6 d[P29, 30] P57L, rPhl p 6 d[29, 30] P79L, rPhl p 6 d[29, 30] P57L P79L, rPhl p 6 d[P29] P30L, rPhl p 6 d[P30] P29L, rPhl p 6 d[P57] P29L P30L, rPhl p 6 d[P79] P29L P30L, rPhl p 6 d[P57, 79] P29L P30L, rPhl p 6 P29L P30L P57L, rPhl p 6 P29L P30L P79L, rPhl p 6 P29L P30L P57L P79Land the like, including all hypoallergenic variants according to the invention described below, are therefore in accordance with the invention, where the numbering follows the sequence of Phl p 6, in particular of ripe Phl p 6.0102.

Here, proline is replaced by way of example by leucine (L). In accordance with the invention, however, the prolines according to the invention can be replaced by any amino acid. Accordingly, all hypoallergenic variants mentioned above in which one or more prolines according to the invention have been substituted by another amino acid are in accordance with the invention. Furthermore, these examples are not restricted to variants of Phl p 6, but also relate, in particular, to Poa p 6 and the group 6 allergens of all other true grasses. However, particular preference is given to all mentioned hypoallergenic variants according to the invention of Phl p 6 of *Phleum pratense*, in particular based on Phl p 6.0102.

T-helper lymphocytes react with peptide fragments of the allergens which form through degradation processes in antigen-presenting cells (APCs) and are presented bound to MHC class II molecules at the surface of the APCs. The peptides generally have a length of 13-18 amino acids, but may also be longer owing to the MHC class 2 binding site which is open laterally. The principal contact points of the peptide with the MHC class molecule are to be found in a core sequence of about 7-10 amino acids. The allergen-specific activation of the T-helper lymphocytes is the prerequisite for proliferation and functional differentiation thereof (for example Treg, $T_H1$ and $T_H2$). The ability of an allergen or allergen variant to stimulate allergen-specific T-lymphocytes is regarded as a key for therapeutic efficacy thereof.

All allergen variants produced on the basis of Phl p 6 or Phl p 6.0102 and described here exhibit substantial retention of crucial T-cell epitopes in experiments.

Thus, variants of group 6 allergens of the Poaceae which have novel protein properties through the modification of proline residues are described for the first time. The proline residues concerned are localised in loop regions. Only the modification of certain proline residues results in the novel variants, which are distinguished by reduced IgE reactivity with substantial retention of the T-cell reactivity and are therefore suitable for curative and preventive specific immunotherapy. Corresponding DNA molecules are suitable for immunotherapeutic vaccination.

The present invention therefore relates to the described allergen variants, DNA molecules and recombinant expression vectors according to the invention as medicaments.

Hypoallergenic variants, DNA molecules and recombinant expression vectors according to the invention or medicaments according to the invention can be used, in particular, for the prophylaxis and/or for the treatment of diseases and conditions. Medicaments according to the invention are particularly suitable for the treatment and/or prophylaxis of type 1 allergies, i.e. for the specific immunotherapy (hyposensitisation) of patients having grass pollen allergy or for the preventive immunotherapy of grass pollen allergies in the triggering of which group 6 allergens of Poaceae species are involved. DNA molecules and recombinant expression vectors according to the invention can be employed for corresponding immunotherapeutic and -prophylactic DNA vaccination.

The invention also relates to the use of at least one hypoallergenic variant according to the invention for the preparation of a medicament for the prevention and/or therapeutic treatment of type 1 allergies in the triggering of which group 6 allergens of the true grasses are causally involved.

Also in accordance with the invention is the use of at least one DNA molecule according to the invention and/or a recombinant expression vector according to the invention, including mixtures thereof in all ratios, for the preparation of a medicament for immunotherapeutic DNA vaccination.

The invention furthermore relates to pharmaceutical preparations comprising at least one hypoallergenic variant according to the invention, at least one DNA molecule according to the invention and/or at least one recombinant expression vector according to the invention, including mixtures thereof in all ratios, and optionally further active compounds and/or assistants for the prevention and/or therapeutic treatment of type 1 allergies.

In particular, pharmaceutical preparations according to the invention are suitable for the prevention and/or therapeutic treatment of type 1 allergies in the triggering of which group 6 allergens of the true grasses are causally involved.

Pharmaceutical preparations in the sense of this invention can be used as therapeutic agents in human or veterinary medicine and can accordingly be administered to humans and animals, in particular mammals, such as monkeys, dogs, cats, rats or mice, and can be used in the therapeutic treatment of the human or animal body and in the combating of the above-mentioned diseases. They can furthermore be used as diagnostic agents or as reagents.

On use of preparations or medicaments according to the invention, the hypoallergenic variants, DNA molecules or recombinant expression vectors according to the invention are generally used analogously to known, commercially available preparations, preferably in doses between 0.001 and 500 mg, in the case of hypoallergenic variants about 1-500 μg, preferably 5-200 μg, per dose in the maintenance phase. The preparation can be administered once or a number of times per day, for example twice, three times or four times per day. The doses are typically increased to the maintenance dose in a dosage-increase phase. Various dosage-increase and maintenance schemes are possible for this purpose. In the case of subcutaneous immunotherapy (SCIT), for example, these may include short-term therapies (limited number of injections before commencement of seasonal complaints, typically 4-7 injections), pre-seasonal therapies (beginning of therapy before the pollen season, typically with weekly injections during the increase phase and monthly injections with the maintenance dose until the beginning of the pollen season) or full-year therapies (dosage-increase phase typically with up to 16 weekly injections followed by monthly injections with the maintenance dose, if necessary reduced dose during the pollen season). In the case of sublingual immunotherapy with aqueous, or solid preparations (tablets, wafers etc.), the therapy can be introduced with or without a dosage-increase phase. The therapy is preferably carried out with daily doses throughout the year, but can also be carried out pre-seasonally or with other application schemes (for example every second day, weekly, monthly).

The expression "effective amount" means the amount of a medicament or pharmaceutical active compound which causes a biological or medical response in a tissue, system, animal or human which is sought or aimed at, for example, by a researcher or physician.

In addition, the expression "therapeutically effective amount" means an amount which, compared with a corresponding subject who has not received this amount, has the following consequence: improved treatment, healing, prevention or elimination of a disease, syndrome, condition, complaint, disorder or prevention of side effects or also the reduction in the progress of a disease, complaint or disorder. The term "therapeutically effective amount" also encompasses the amounts which are effective in increasing normal physiological function.

Medicaments can be adapted for administration via any desired suitable route, for example by oral (including buccal or sublingual), rectal, pulmonary, nasal, topical (including buccal, sublingual or transdermal), vaginal or parenteral (including subcutaneous, intramuscular, intravenous or intradermal) routes. Such medicaments can be prepared using all processes known in the pharmaceutical area, for example by combining the active compound with the excipient(s) or assistant(s).

Suitable for parenteral use are, in particular, solutions, preferably oily or aqueous solutions, furthermore suspensions, emulsions or implants. The allergen variants according to the invention can also be lyophilised and the resultant lyophilisates used, for example, for the preparation of injection preparations. The preparations indicated may be sterilised and/or comprise adjuvants, such as lubricants, preservatives, stabilisers and/or wetting agents, emulsifiers, salts for modifying the osmotic pressure, buffer substances and/or a plurality of further active compounds. Furthermore, depot preparations can be obtained by corresponding formulation of the allergen variants according to the invention, for example by adsorption onto aluminium hydroxide, calcium phosphate or tyrosine.

Suitable excipients are organic or inorganic substances which are suitable for parenteral administration and do not react with group 6 allergen variants according to the invention. Examples thereof are excipients such as water, vegetable oils, benzyl alcohols, polyethylene glycols, glycerol triacetate, gelatine, carbohydrates, such as lactose or starch, magnesium stearate, talc, lanolin or Vaseline.

Parenteral administration is preferably suitable for the administration of the medicaments according to the invention. In the case of parenteral administration, intravenous, subcutaneous, intradermal or intralymphatic administration are particularly preferred. In the case of intravenous administration, the injection can take place directly or as an addition to infusion solutions.

Medicaments which are adapted to parenteral administration include aqueous and non-aqueous sterile injection solutions, which comprise antioxidants, buffers, bacteriostatics and solubilisers by means of which the formulation is rendered isotonic with the blood of the recipient to be treated, and aqueous and non-aqueous sterile suspensions, which may comprise suspension agents and thickeners. The formulations can be administered in single-dose or multidose containers, for example sealed ampoules and vials, and stored in freeze-dried (lyophilised) state, meaning that only the addition of the sterile carrier liquid, for example water for injection purposes, immediately before use is necessary. Injection solutions and suspensions prepared in accordance with the formulation can be prepared from sterile powders, granules and tablets.

If desired, preparations or medicaments according to the invention may comprise one or more further active compounds and/or one or more action enhancers (adjuvants).

The present invention thus furthermore relates to pharmaceutical preparations comprising further active compounds and/or assistants. The invention preferably relates to pharmaceutical preparations according to the invention, characterised in that the further active compounds are allergens or variants thereof. Examples of suitable further active compounds are other allergens, in particular allergens of the true grasses, particularly preferably allergens from the Pooideae sub-family, preferably from the groups Poodae and Triticodae, preferably represented by *Phleum pratense, Holcus lanatus, Phalaris aquatica, Dactylis glomerata, Lolium perenne, Poa pratensis, Hordeum vulgare, Secale cereale* and *Triticum aestivum*, for example group 1, 2, 3, 4, 5, 6, 7, 10, 12 or 13 allergens and variants thereof, for example hypoallergenic variants, fragments, multimers, hybrid molecules or recombinant fusion proteins. The present invention furthermore relates to pharmaceutical preparations comprising at least one further assistant, particularly preferably so-called adjuvants. Examples of adjuvants are aluminium hydroxide, monophosphoryl lipid A, activators of Toll-like receptors, such as, for example, lipopolysaccharides and CpG oligonucleotides, vitamin D3, mycobacterial antigens and molecules from parasites (for example schistosomes or filariae), such as, for example, Cystatin or ES-62.

The invention also relates to sets (kits) consisting of separate packs of a) a pharmaceutical preparation according to the invention comprising an effective amount of a hypoallergenic variant, DNA molecule or recombinant expression vector according to the invention b) a pharmaceutical preparation comprising an effective amount of a further pharmaceutical active compound and/or adjuvant.

The set contains suitable containers, such as boxes or cartons, individual bottles, bags or ampoules. The set may contain, for example, separate ampoules each containing a formulation according to the invention comprising an effective amount of a hypoallergenic variant, DNA molecule or recombinant expression vector according to the invention and a formulation of a further medicament active compound in dissolved or lyophilised form.

Even without further embodiments, it is assumed that a person skilled in the art will be able to utilise the above description in the broadest scope. The preferred embodiments should therefore merely be regarded as descriptive disclosure, which is, however, in no way limiting in any way.

The following examples are thus intended to explain the invention without limiting it. Unless indicated otherwise, percent data mean percent by weight. All temperatures are indicated in degrees Celsius. "Conventional work-up": water is added if necessary, the pH is adjusted, if necessary, to values between 2 and 10, depending on the constitution of the end product.

The following hypoallergenic variants according to the invention were prepared by biotechnological methods and characterised. However, the preparation and characterisation of the substances can also be carried out by other methods for the person skilled in the art. For example, the hypoallergenic variants according to the invention can also be synthesised chemically. The invention likewise relates to the hypoallergenic variants according to the invention described below.

BRIEF DESCRIPTION OF THE DRAWINGS

FIG. 1 shows the alignment of the deduced amino acid sequences of Group 6 and Group 5 allergens of Timothy grass. The amino acid sequences of two Phl p 6 isoforms [Phl p 6.0101 (UniprotKB O65868; SEQ ID NO: 4) and Phl p 6.0102 (UniprotKB P43215; SEQ ID NO: 2)] and four Phl p 5 isoforms [Phl p 5.0101 (UniprotKB Q40960; SEQ ID NO: 11), Phl p 5.0104 (UniprotKB P93467; SEQ ID NO: 12), Phl p 5.0109 (UniprotKB Q84U12; SEQ ID NO: 13) and Phl p 5.0201 (UniprotKB Q40963; SEQ ID NO: 14)

FIG. 2 (*a*) and (*b*) show a working model of the 3D structure of Phl p 6. FIG. 2(*a*) shows that four α-helices (H1-H4) form a 4-helix bundle, wherein proline residues 29, 30, 57 and 79 are present in the loops connecting the helices and proline 101 is located behind the final helix. FIG. 2(*b*) shows a surface model of Phl p 6, wherein the proline residues 29, 30, 57, 79 and 101 are exposed at the surface.

FIG. 3 shows the cDNA sequence of Phl p 6 wt (Phl p 6.0102). The 330 bp cDNA sequence accessioned in GenBank as Y16955 has the sequence set forth in SEQ ID NO: 1.

FIG. 4 shows the deduced amino acid sequence of Phl p 6 wt (Phl p 6.0102). The 110 amino acid sequence accessioned in UniProtKB as O65868 has the sequence set forth in SEQ ID NO:2.

FIG. 5 shows the DNA sequence (33 bp) of the N terminal histidine fusion component, having the sequence set forth in SEQ ID NO: 5.

FIG. 6 shows the amino acid sequence (11 amino acids) of the N terminal histidine fusion component, having the sequence set forth in SEQ ID NO: 6.

FIG. 7 shows resolution of various polypeptides in 12% SDS-PAGE. The samples (~1 μg of protein per track, non-reduced) are as follows: Lane 1=rPhl p 6 wt+6His; Lane 2=d[P29, 30]+6His; Lane 3=d[P57]+6His; Lane 4=d[P79]+6His; Lane 5=d[P101]+6His. Lane M: size marker.

FIG. 8 shows a chromatogram of an analytical SEC with online molecular weight determination of various Phl p 6 variants with proline mutations in a loop. Panel 1=rPhl p 6 wt+6His; Panel 2=d[P29, 30]+6His; Panel 3=d[P57]+6His; Panel 4=d[P79]+6His; Panel 5=d[P101]+6His.

FIG. 9 shows IgE binding of immobilized Phl p 6 variants with proline deletions in a loop. Recombinant Phl p 6 (rPhl p 6 wt), proline deletion variants thereof with histidine fusion component (+6His) and without histidine fusion component were incubated with sera of clinically defined grass pollen allergy sufferers (3-150). Human serum albumin (HSA) was used as a negative control. The "Total" column represents a control for uniform protein charging of the test strips, which shows staining with reagent "DB71" (Sigma-Aldrich, Taufkirchen).

FIG. 10 shows IgE inhibition test of Phl p 6 variants with proline deletions in a loop. Top panel shows results of experiments with pollen allergy sufferer-32 (P32); bottom panel shows results of experiments with pollen allergy sufferer-82 (P82).

FIG. 11 shows results of a test for functional allergeneity of the proline mutants with mutations in individual loops.

FIG. 12 shows resolution of Phl p 6 variants with proline mutations in two or three loops (with 12% SDS-PAGE). The samples (~1 μg of protein per track, non-reduced) are as follows: Lane 1=d[29, 30, 57]+6His; Lane 2=d[P29, 30, 79]+6His; Lane 3=d[P29, 30] P57L+6His; Lane 4=d[P29, 30] P79L+6His; Lane 5=d[P29, 30] P57L, P79L]+6His. Lane M: size marker.

FIG. 13 shows a chromatogram of an analytical SEC with online molecular weight determination of various Phl p 6 variants with proline mutations in two or three loops.

FIG. 14 shows IgE binding of recombinant Phl p 6 wild-type (rPhl p6 wt) or variants thereof with proline deletions in one, two or three loops. Recombinant Phl p 6 (rPhl p 6 wt), proline deletion variants thereof with histidine fusion component (+6His) and without histidine fusion component were incubated with sera of clinically defined grass pollen allergy sufferers (3-150). Human serum albumin (HSA) was used as a negative control. The "Total" column represents a control for uniform protein charging of the test strips, which shows staining with reagent "DB71" (Sigma-Aldrich, Taufkirchen).

FIG. 15 shows cDNA sequence (GenBank entry: Z27082.1; 330 bp) of Phl p 6 wt (IUIS entry Phl p 6.0101), which is set forth as SEQ ID NO: 3.

FIG. 16 shows deduced amino acid sequence (UniProtKB entry: P43215; 110 aa) of Phl p 6 wt (IUIS entry Phl p 6.0101), which is set forth as SEQ ID NO: 4.

FIG. 17: shows amino acid sequence of the variant of Phl p 6.0101 (UniProtKB entry O65869; 107 aa), which is set forth as SEQ ID NO: 7. In the variant is represented by an italic L, the first three amino acids are missing.

FIG. 18: shows amino acid sequence of the variant of Phl p 6.0101 (incl. propeptide), according to the sequencing results of the instant application (Propeptide component and Y to H variant are represented by bold italics). The sequence is set forth in SEQ ID NO: 8.

FIG. 19: shows amino acid sequence of pro Phl p 6.0101 (P43215) (propeptide component is represented by bold and italics). The sequence is set forth in SEQ ID NO: 9.

FIG. 20: shows amino acid sequence of pro Phl p 6.0102 (O65868) (propeptide component is represented by bold and italics). The sequence is set forth in SEQ ID NO: 10.

EXAMPLE 1

Variants of Phl p 6 with Proline Deletions in a Single Loop Region

The preparation of variants rPhl p 6 d[P29, 30]+6His, rPhl p 6 d[P57]+6His, and rPhl p 6 d[P79]+6His and immunological characterisation thereof is described below. The recombinant unmodified allergen (rPhl p 6 wt+6His) is prepared and investigated analogously, and the hypoallergenic variants of the other group 6 allergens according to the invention of the true grasses and their wild-type proteins, in particular Poa p 6, can also be prepared and investigated analogously.

Construction by Genetic Engineering:

The DNAs encoding for the variants are synthesised by the bonding of long overlapping DNA oligonucleotides and amplification of the DNA by a PCR standard method. The codons are selected so concentration of a particle is determined by the RI detector, and the light scattering by the particle is recorded by the MALS detector (Wen et al., 1996, Anal. Biochem. 240:155-166). The average mass of the eluted particles can be calculated from these data with an accuracy of about 5%. Monomers, dimers other multimers and aggregates can be detected by SEC/MALS/RI.

In the SEC/MALS/RI analysis, it becomes clear that the proteins which each elute in a single peak are in the form of pure monomers under native conditions (FIG. 8; Table 1).

TABLE 1

Molecular weight of Phl p 6 wild type and Phl p 6 variants with proline deletions in loops 1, 2, 3 or 4

| Samples | Protein | $MW_{calc.}$[1] [kD] | SEC[2] MW [kD] | Assessment |
|---|---|---|---|---|
| 1 | Phl p 6 wt + 6His | 12.92 | 12.89 | Monomer |
| 2 | d[P29, 30] + 6His | 12.73 | 12.88 | Monomer |
| 3 | d[P57] + 6His | 12.83 | 12.91 | Monomer |
| 4 | d[P79] + 6His | 12.83 | 12.92 | Monomer |
| 5 | d[P101] + 6His | 12.83 | 12.89 | Monomer |

[1]Calculated molecular weight on the basis of the amino acid sequence with starting methionine (software: EditSeq 6.0; DNA-Star Inc., Madison, USA).
[2]Determination of the particle mass by gel filtration (SEC). The average mass of the eluted protein particles in the peak window set is indicated.

The online determination of the protein concentration was carried out using the OptilabrEX refractive index detector (RI) (Wyatt, Santa Barbara, USA). The light scattering by the particles was determined using the MiniDAWN Treos (Wyatt) multiangle detector. The particle mass was calculated using the ASTRA 5.3.2.17 software (Wyatt) via Debeye formalism with an assumed refractive index increment of 0.180 ml/g. SEC column: Superdex 200 GL 10/300 (GE Healthcare, Uppsala, Sweden). Eluent: 20 mM sodium phosphate buffer pH 7.2 with 150 mM NaCl.

that the deduced amino acid sequence is based on that of ripe Phl p 6.0102 (FIG. 3, FIG. 4). The mutations for the proline deletions are introduced using specific oligonucleotides which lack the corresponding codons for proline in the PCR reactions. These oligonucleotides are selected so that the deduced protein carries a hexahistidine fusion component at the 5' end (FIG. 5, FIG. 6).

These DNAs ligated into expression vector pTrcHis2 Topo (Invitrogen, Carlsbad, USA) via a topoisomerase reaction. The correctness of the DNA is confirmed by sequencing.

Expression and Purification:

The expression of the recombinant histidine fusion proteins is carried out in *Escherichia coli* (Top10 strain; Invitrogen). rPhl p 6 wt+6 His and the variants are primarily purified by specific binding of the N-terminal histidine residues to an Ni2+ chelate matrix (immobilised metal ion affinity chromatography, IMAC; material: HiTrap, GE Healthcare, Uppsala, Sweden). The recombinant proteins from thel MAC eluate are subsequently concentrated and a gel filtration is carried out (material: Superdex 75; GE Healthcare).

Biochemical Analysis:

The purity of the proteins prepared is firstly checked by an SDS-PAGE with subsequent Coomassie staining. The analysis shows a very high degree of purity of all proteins (FIG. 7).

Analytical gel filtration (SEC) allows the separation of protein species on the basis of their specific hydrodynamic radii. An online determination of the molecular weight can be achieved by coupling a refractometer (RI detector) and a multiangle light scattering detector (MALS detector) to the chromatography system (SEC/MALS/RI method). In this method, the given at the measurement time The absence of insoluble protein aggregates is also checked by UV-Vis spectroscopy (photometer: Ultrospec 5300pro UV/VIS; GE Healthcare).

In the UV-Vis spectroscopy, a wave spectrum of the protein solution is recorded in the wave range from 240-800 nm. Insoluble aggregates in protein solutions absorb in the wavelength range >300 nm, while highly soluble proteins do not absorb in this range. The wave spectra are typical of proteins having high solubility. The proteins according to the invention are thus soluble, highly pure and monomeric under native conditions.

Evidence of Reduced IgE Binding:

A simple test method for the determination of the reactivity of specific IgE from allergy sufferer sera is the strip test. Using this method, a relatively large number of allergy sufferer sera can be investigated in parallel.

For this purpose, the test substances in identical concentration and amount are bound alongside one another to a strip of nitrocellulose membrane under non-denaturing conditions. A series of such membrane strips can be incubated in parallel with different allergy sufferer sera. After a washing step, the specifically bound IgE antibodies become visible on the membrane through a colour reaction promoted by an anti-human IgE/alkaline phosphatase conjugate.

The results with the Phl p 6 variants using 18 individual grass pollen allergy sufferer sera are depicted in FIG. 9. As an important control, firstly the IgE binding of the recombinant allergen with and without histidine fusion component is investigated. Both proteins exhibit the same IgE binding ability. The N-terminal histidine fusion component used for the studies accordingly does not interfere with the binding of IgE to Phl p 6.

Mutant rPhl p 6 d[P101]+6His exhibits similarly good IgE binding as the unmodified allergen with all sera tested (FIG. 9). It follows from this that deletion of proline 101 has no significant influence on the IgE binding ability of Phl p 6. The IgE binding of mutants rPhl p 6 d[P29, 30]+6His, rPhl p 6 d[P57]+6His and rPhl p 6 d[P79]+6His is different in the sera of different grass pollen allergy sufferers. This is due to variations in the composition of the IgE population of individual allergy sufferers with respect to affinity and epitope specificity of the IgE antibodies. Mutants rPhl p 6 d[P57]+6His and rPhl p 6 d[P79]+6His exhibit significantly reduced IgE reactivity with most sera compared with unmodified rPhl p 6 wt+6H is. However, the lowest IgE binding is observed throughout in the case of mutant rPhl p 6 d[P29, 30]+6His (FIG. 9).

The investigation of the IgE binding ability of dissolved test substances is carried out using an EAST inhibition test (enzyme allergosorbent test). In this method, the allergen/IgE interaction can be investigated in solution, enabling interfering masking of epitopes of the test substance to be excluded, for example by immobilisation on a membrane.

The EAST inhibition test is carried out as follows. Microtitre plates are coated with the allergens, here rPhl p 6 wt+6H is. After removal of the unbound allergen molecules by washing, the plate is blocked with bovine serum albumin in order to prevent later non-specific binding. IgE antibodies of allergy sufferers as individual sera in suitable dilution were incubated with the allergen-coated microtitre plates. The amount of allergen-bound IgE antibodies is quantified photometrically via an Anti-hIgG/alkaline phosphatase conjugate by the reaction of a substrate to give a coloured end product.

The binding of the IgE antibodies is inhibited substance-specifically by a soluble allergen or the substance to be tested (recombinant modified allergen) as a function of the concentration.

The IgE inhibition test results depicted in FIG. 10 with the recombinant allergen variants of Phl p 6 show that deletion of proline residues P[29, 30], P57 and P79 causes reduced IgE binding ability of Phl p 6. The IgE binding ability of mutant d[P29, 30] is significantly lower than that of d[P57] or d[P79]. A lower inhibitory action indicates a loss of IgE epitopes. Mutant d[P101] does not exhibit modified IgE binding with the serum of grass pollen allergy sufferer P32 and only slightly reduced binding with serum P82, which again approximates to that of the wild type at high inhibitor concentration.

Evidence of the Reduction of the Functional Allergeneity:

The functional action of mutants in the crosslinking of membrane-bound IgE of the effector cells and activation thereof is subsequently investigated in vitro.

For the basophil activation test, heparinised whole blood of grass pollen allergy sufferers is incubated with various concentrations of the test substances. Allergenic substances are able to bind specific IgE antibodies which are associated with the high-affinity IgE receptors of the basophilic granulocytes. The crosslinking of the IgE/receptor complexes triggered by the allergen molecules results in signal transduction, which results in degranulation of the effector cells and thus the triggering of the allergic reactions in vivo.

The allergen-induced activation of basophilic immunocytes can be determined in vitro by quantification of the expression of a surface protein (CD203c) coupled to the signal transduction of IgE-receptor crosslinking (Kahlert et al., Clinical Immunology and Allergy in Medicine Proceedings of the EAACI-2002 (2003) Naples, Italy 739-744). The number of surface proteins expressed on a cell and the percentage value of the activated cells of a cell pool is measured highly sensitively via the binding of a fluorescence-labelled monoclonal antibody to the surface protein and subsequent analysis by fluorescence-activated flow cytometry.

The granulocytes employed in the test are in the present example isolated from the whole blood of allergy sufferer P21. This allergy sufferer represents those allergy sufferers whose IgE antibodies exhibit detectable binding to rPhl p 6 d[P29, 30]+6His in the strip test method (group "A").

At the same concentration of unmodified, recombinant allergen and of rPhl p 6 d[P29, 30]+6His, the latter exhibits lower binding to membrane-bound IgE antibodies in the case of both donors and consequently drastically reduced activation of basophilic granulocytes (FIG. 11.).

The results thus confirm functionally reduced allergeneity of mutant rPhl p 6 d[P29, 30]+6H is. Mutants rPhl p 6 d[P57]+6His and rPhl p 6 d[P79]+6His exhibit clearly reduced activation of the basophil cells in the case of donor P21. It can thus be confirmed with this test that proline mutations in these two regions of Phl p 6 also reduces the IgE binding ability, at least in some allergy sufferers.

T-Cell Reactivity of the Variants:

In order to investigate the T-cell reactivity, oligoclonal T-cell lines of grass pollen allergy sufferers are established by conventional methods with stimulation by the unmodified allergen. In a proliferation test, the different T-cell lines are stimulated by the reference allergen rPhl p 6 wt and the modified recombinant allergen variants. The proliferation rate is determined by conventional methods by the incorporation of [3H]-thymidine.

Variants rPhl p 6 d[P29, 30]+6His, rPhl p 6 d[57]+6His and rPhl p 6 d[79]+6His stimulate into the investigated T-cell lines to a comparable extent for proliferation by the unmodified allergen. Retention of the important T-cell epitopes can be concluded from this.

EXAMPLE 2

Variants of Phl p 6 with Combinations of Proline Deletions in a Number of Loop Regions The preparation and immunological characterisation of variants rPhl p 6 d[P29, 30, 57]+6His and rPhl p 6 d[29, 30, 79]+6His is described below by way of example for hypoallergenic variants of group 6 allergens of the Poaceae with combinations of proline deletions corresponding to the amino acid positions in Phl p 6 wild type NIS entry Phl p 6.0102) 29, 30; 57 and 79.

The deleted proline residues can be located here in two or three of the loop regions homologous to Phl p 6. The corresponding hypoallergenic variants of Phl p 6 wild-type isomer Phl p 6.0101 (GenBank: Z27082.1, UniProt: P43215) are prepared and investigated analogously, and the hypoallergenic variants of the other group 6 allergens according to the invention of the true grasses and their wild-type proteins, in particular Poa p 6, can also be prepared and investigated analogously.

The codons are selected so that the deduced amino acid sequence is based on that of ripe Phl p 6.0102 (FIG. 3, FIG. 4). The mutations for the proline deletions are introduced using specific oligonucleotides which lack the corresponding codons for proline in the PCR reactions. The oligonucleotides are preferably selected so that the deduced protein carries a hexahistidine fusion component at the 5' end (FIG. 5, FIG. 6). The DNAs are ligated into expression vector pTrcHis2 Topo (Invitrogen, Carlsbad, USA) via a topoisomerase reaction. The correctness of the DNA is confirmed by sequencing. However, other standard expression vectors can also be used.

The expression of the recombinant histidine fusion proteins can be carried out in all standard eukaryotic and prokaryotic expression systems, the expression is preferably carried out in *Escherichia coli* (Top10 strain; Invitrogen). The variants are primarily purified by the specific binding of the N-terminal histidine residues to an $Ni^{2+}$ chelate matrix (immobilised metal ion affinity chromatography, IMAC; material: HiTrap, GE Healthcare, Uppsala, Sweden). The recombinant proteins are subsequently concentrated from the IMAC eluate, and a gel filtration is carried out (material: Superdex 75; GE Healthcare).

Biochemical Analysis:

The purity of the proteins prepared is firstly checked by an SDS-PAGE with subsequent Coomassie staining. The analysis showed a very high degree of purity of all proteins (FIG. 12).

Analytical SEC, in which the proteins are investigated under native conditions, shows that the proteins elute in a single peak. High-molecular-weight aggregates are not detected (FIG. 13.). The online determination of the molecular weight by MALS/RI leads to the result that rPhl p 6 d[29, 30, 79]+6His is in purely monomeric form, while the eluted rPhl p 6 d[P29, 30, 57]+6His represents a mixture of monomers and dimers (FIG. 13; Table 2). However, the wave spectra of both proteins recorded by UV-Vis spectroscopy are typical of proteins having high solubility.

Both proteins are thus soluble, pure and free from precipitates under native conditions and thus meet the essential prerequisites for precise analysis of their specific IgE binding ability.

TABLE 2

Molecular weight of Phl p 6 mutants with mutations in a number of loops

| Sample | Protein | $MW_{calc.}$[1] [kD] | SEC/ MALS/RI[2] MW [kD] | Assessment |
|---|---|---|---|---|
| 1 | d[P29, 30, 57] + 6His | 12.63 | 17.24 | Monomer/ dimer mixture |
| 2 | d[P29, 30, 79] + 6His | 12.63 | 12.82 | Monomer |
| 3 | d[P29, 30] P57L + 6His | 12.75 | 20.95 | Monomer/ dimer mixture |
| 4 | d[P29, 30] P79L + 6His | 12.75 | 12.99 | Monomer |
| 5 | d[P29, 30] P57L P79L + 6His | 12.76 | 25.56 | Predominantly dimers |

[1]Calculated molecular weight on the basis of the amino acid sequence with starting methionine (software: EditSeq 6.0; DNA-Star Inc., Madison, USA).

[2]Determination of the particle mass by gel filtration (SEC). The average mass of the eluted protein particles in the peak window set is indicated.

The online determination of the protein concentration was carried out using the OptilabrEX refractive index detector (RI) (Wyatt, Santa Barbara, USA). The light scattering by the particles was determined using the MiniDAWN Treos (Wyatt) multiangle detector. The particle mass was calculated using the ASTRA 5.3.2.17 software (Wyatt) via Debeye formalism with an assumed refractive index increment of 0.180 ml/g. SEC column: Superdex 200 GL 10/300 (GE Healthcare, Uppsala, Sweden). Eluent: 20 mM sodium phosphate buffer pH 7.2 with 150 mM NaCl.

Evidence of Reduced IgE Binding:

The results of a strip test with rPhl p 6 d[P29, 30, 57]+6His and rPhl p 6 d[29, 30, P79]+6His using 18 individual grass pollen allergy sufferer sera are depicted in FIG. 14. Surprisingly, it is apparent that the sera of allergy sufferers which still have detectable IgE binding to rPhl p 6 d[P29, 30] in the strip test have predominantly massively reduced IgE reactivity with variants rPhl p 6 d[P29, 30, 57]+6His and rPhl p 6 d[29, 30, 79]+6His (group "A": sera 21, 32, 83, 137 etc.).

It is thus clearly shown that the IgE binding ability of Phl p 6 can be reduced further by a plurality of combined deletions of prolines from various loop regions than is possible through the deletion of proline residues in only one single loop region.

T-Cell Reactivity of the Variants:

The variants stimulate the proliferation of the investigated T-cell lines to a comparable extent as the unmodified allergen. Retention of the important T-cell epitopes can be concluded from this.

EXAMPLE 3

Variants of Phl p 6 with Combinations of Proline Point Mutations in a Number of Loop Regions The preparation and immunological characterisation of variants rPhl p 6 d[P29, 30] P57L+6His, rPhl p 6 d[29, 30] P79L+6His and rPhl p 6 d[29, 30] P57L P79L+6His is described below by way of example for hypoallergenic variants of group 6 allergens of the Poaceae with combinations of proline point mutations corresponding to the amino acid positions in Phl p 6 wild type NIS entry Phl p 6.0102) 29, 30 57 and 79. The proline residues can be converted into any amino acid. The corresponding hypoallergenic variants of Phl p 6 wild-type isomer Phl p 6.0101 (GenBank: Z27082.1, UniProt: P43215) are prepared and investigated analogously, and the hypoallergenic variants of the other group 6 allergens according to the invention of the true grasses and their wild-type proteins, in particular Poa p 6, can also be prepared and investigated analogously.

The codons are selected so that the deduced amino acid sequence is based on that of ripe Phl p 6.0102 (FIG. 3, FIG. 4). The mutations for the proline deletions are introduced using specific oligonucleotides which lack the corresponding codons for proline in the PCR reactions. The oligonucleotides are preferably selected so that the deduced protein carries a hexahistidine fusion component at the 5' end (FIG. 5, FIG. 6).

The DNAs are ligated into expression vector pTrcHis2 Topo (Invitrogen, Carlsbad, USA) via a topoisomerase reaction. The correctness of the DNA was confirmed by sequencing. However, other standard expression vectors can also be used.

The expression of the recombinant histidine fusion proteins can be carried out in all standard eukaryotic and prokaryotic expression systems, the expression is preferably carried out in *Escherichia coli* (Top10 strain; Invitrogen). The variants are primarily purified by the specific binding of the N-terminal histidine residues to an $Ni^{2+}$ chelate matrix (immobilised metal ion affinity chromatography, IMAC; material: HiTrap, GE Healthcare, Uppsala, Sweden). The recombinant proteins are subsequently concentrated from the IMAC eluate, and a gel filtration is carried out (material: Superdex 75; GE Healthcare).

Biochemical Analysis:

The purity of the proteins prepared is firstly checked by an SDS-PAGE with subsequent Coomassie staining. The analysis shows a very high degree of purity of all proteins (FIG. 12).

Analytical SEC, in which the proteins are investigated under native conditions, shows that the proteins elute in a single peak. High-molecular-weight aggregates are not detected (FIG. 13.) The online determination of the molecular weight by MALS/RI leads to the result that rPhl p 6 d[29, 30] P79L+6His is in purely monomeric form, while the eluted rPhl p 6 d[P29, 30] P57L+6His represents a mixture of monomers and dimers. rPhl p 6 d[29, 30] P57L P79L+6His is predominantly in the form of the dimer (FIG. 13; Table 2.

The wave spectra of all proteins recorded by UV-Vis spectroscopy are typical of proteins having high solubility. The three proteins are thus soluble, pure and free from precipitates under native conditions and thus meet the essential prerequisites for precise analysis of their specific IgE binding ability.

Evidence of Reduced IgE Binding:

The results of a strip test with rPhl p 6 d[P29, 30] P57L+6His, rPhl p 6 d[29, 30] P79L+6His and rPhl p 6 d[29, 30] P57L P79L+6His using 18 individual grass pollen allergy sufferer sera are depicted in FIG. 12.

Surprisingly, it is apparent that the sera of allergy sufferers which still have detectable IgE binding to rPhl p 6 d[P29, 30] in the strip test have predominantly massively reduced IgE reactivity with variants rPhl p 6 d[P29, 30] P57L+6His, rPhl p 6 d[29, 30] P79L+6His and rPhl p 6 d[29, 30] P57L P79L+6His (group "A": sera 21, 32, 83, 137 etc.).

It is thus clearly shown that the IgE binding ability of Phl p 6 can be reduced further by a plurality of combined point mutations of prolines from various loop regions than is possible through the point mutation of proline residues in only a single loop region.

T-Cell Reactivity of the Variants:

The variants stimulate the proliferation of the investigated T-cell lines to a comparable extent as the unmodified allergen. Retention of the important T-cell epitopes can be concluded from this.

We claim:

1. A variant of a group 6 allergen of the true grass family (Poaceae) comprising a polypeptide sequence having at least 95% sequence identity to the wild-type Phl p 6 of SEQ ID NO: 2 and having a deletion or a substitution of at least one proline in position 29, 30, 57, or 79 in said SEQ ID NO: 2.

2. The variant of a group 6 allergen of the true grass family (Poaceae) of claim 1, comprising the polypeptide sequence of SEQ ID NO: 2 with the proviso that at least one proline in said SEQ ID NO: 2 is substituted by another amino acid.

3. A fusion protein or a multimer comprising the variant of a group 6 allergen of the true grass family (Poaceae) of claim 1.

4. A medicament comprising the variant of a group 6 allergen of the true grass family (Poaceae) of claim 1 and a carrier.

5. A method for the reducing the incidence of or treating type 1 allergies, comprising administering to a subject in need thereof, a medicament according to claim 4.

6. A pharmaceutical preparation comprising the variant of a group 6 allergen of the true grass family (Poaceae) of claim 1 and a pharmaceutically acceptable carrier.

7. The pharmaceutical preparation according to claim 6, further comprising an allergen of true grass or a variant thereof.

8. The variant of a group 6 allergen of the true grass family (Poaceae) of claim 1, which is a recombinant protein.

9. The variant of a group 6 allergen of the true grass family (Poaceae) of claim 1, comprising deletion of at least one proline in positions 29, 30, 57, or 79 in said SEQ ID NO: 2.

10. The variant of a group 6 allergen of the true grass family (Poaceae) of claim 2, with the proviso that at least one proline in said SEQ ID NO: 2 is substituted by leucine or alanine.

* * * * *